United States Patent
Ogi

(10) Patent No.: US 11,774,742 B2
(45) Date of Patent: Oct. 3, 2023

(54) OPTICAL UNIT FOR ENDOSCOPE AND ENDOSCOPE

(71) Applicant: OLYMPUS CORPORATION, Tokyo (JP)

(72) Inventor: Shun Ogi, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 466 days.

(21) Appl. No.: 16/906,522

(22) Filed: Jun. 19, 2020

(65) Prior Publication Data

US 2020/0319448 A1  Oct. 8, 2020

Related U.S. Application Data

(63) Continuation of application No. PCT/JP2018/032818, filed on Sep. 5, 2018.

(30) Foreign Application Priority Data

Dec. 22, 2017  (JP) ................................. 2017-247013

(51) Int. Cl.
   *G02B 23/24* (2006.01)
   *A61B 1/00* (2006.01)
   *G02B 7/04* (2021.01)

(52) U.S. Cl.
   CPC ........ *G02B 23/243* (2013.01); *A61B 1/00158* (2013.01); *A61B 1/00188* (2013.01); *A61B 1/00195* (2013.01); *G02B 7/04* (2013.01)

(58) Field of Classification Search
   CPC ............ A61B 1/00195; A61B 1/00158; A61B 1/00188; G02B 23/2423; G02B 23/243; G02B 7/04; G02B 23/2469; H02K 33/16
   See application file for complete search history.

(56) References Cited

U.S. PATENT DOCUMENTS 5,138,497 A * 8/1992 Blanding ............. G11B 7/0932
                                        359/823
5,499,143 A * 3/1996 Sakamoto ................ G02B 7/08
                                        359/822

(Continued)

FOREIGN PATENT DOCUMENTS

JP  2016-206408 A  12/2016
JP  2017-063845 A   4/2017

(Continued)

OTHER PUBLICATIONS

International Search Report dated Oct. 30, 2018 issued in PCT/JP2018/032818.

*Primary Examiner* — John P Leubecker
*Assistant Examiner* — Jae Woo
(74) *Attorney, Agent, or Firm* — Scully, Scott, Murphy & Presser, P.C.

(57) ABSTRACT

An optical unit for endoscope includes: a moving barrel which is a soft magnetic body, configured to hold a lens; a fixed barrel which is a non-magnetic body, configured to movably hold the moving barrel on an inner circumferential face; a pair of yokes arranged on an outer face of the fixed barrel; a coil wound around the outer face of the fixed barrel and a magnet arranged on a part in the circumferential direction, between the pair of yokes; and a magnetic body member with magnetism stronger than magnetism of the moving barrel, the magnetic body member being arranged on a part of the moving barrel in the circumferential direction, corresponding to the magnet.

20 Claims, 12 Drawing Sheets

(56) References Cited

U.S. PATENT DOCUMENTS

| | | | |
|---|---|---|---|
| 5,541,777 A * | 7/1996 | Sakamoto | G02B 7/102 |
| | | | 310/13 |
| 7,859,144 B1 * | 12/2010 | Sahyoun | H02K 33/16 |
| | | | 335/229 |
| 8,084,898 B2 * | 12/2011 | Kawano | H02K 7/06 |
| | | | 310/152 |
| 8,264,104 B2 | 9/2012 | Schrader | |
| 8,449,274 B1 * | 5/2013 | Zelechonok | F04B 17/04 |
| | | | 417/419 |
| 8,643,228 B2 | 2/2014 | Vogel | |
| 8,922,067 B2 | 12/2014 | Vogel | |
| 8,946,947 B2 | 2/2015 | Kelp | |
| 9,722,480 B2 | 8/2017 | Kelp | |
| 9,924,854 B2 * | 3/2018 | Iwasaki | A61B 1/00 |
| 10,003,747 B2 * | 6/2018 | Morinaga | H04N 5/2251 |
| 10,101,457 B1 * | 10/2018 | Topliss | G01S 7/4817 |
| 2005/0057101 A1 * | 3/2005 | Nakagawa | H02K 33/16 |
| | | | 310/12.24 |
| 2006/0138873 A1 * | 6/2006 | Yasuda | G02B 7/102 |
| | | | 359/701 |
| 2007/0019307 A1 * | 1/2007 | Suemori | G02B 7/102 |
| | | | 359/811 |
| 2011/0210690 A1 * | 9/2011 | Vogel | G02B 23/2476 |
| | | | 310/14 |
| 2013/0193778 A1 * | 8/2013 | Wieters | H02K 41/02 |
| | | | 310/12.04 |
| 2016/0018625 A1 * | 1/2016 | Morishima | H02K 7/14 |
| | | | 359/824 |
| 2018/0031800 A1 * | 2/2018 | Iguchi | G02B 7/08 |
| 2018/0049621 A1 * | 2/2018 | Iguchi | A61B 1/00096 |
| 2019/0280582 A1 * | 9/2019 | Wieters | G02B 7/08 |
| 2020/0000324 A1 * | 1/2020 | Wieters | H02K 41/031 |
| 2022/0320931 A1 * | 10/2022 | Hatano | H01F 7/1646 |

FOREIGN PATENT DOCUMENTS

| | | |
|---|---|---|
| JP | 2017-111193 A | 6/2017 |
| WO | WO 2019/026445 A1 | 2/2019 |
| WO | WO 2019/187188 A1 | 10/2019 |

* cited by examiner

OPTICAL UNIT FOR ENDOSCOPE AND ENDOSCOPE

CROSS REFERENCE TO RELATED APPLICATION

This application is a continuation application of PCT/JP2018/032818 filed on Sep. 5, 2018 and claims benefit of Japanese Application No. 2017-247013 filed in Japan on Dec. 22, 2017, the entire contents of which are incorporated herein by this reference.

BACKGROUND OF INVENTION

1. Field of the Invention

The present invention relates to an optical unit for endoscope that moves an optical device using a coil and a magnet, and an endoscope provided with the optical unit for endoscope.

2. Description of the Related Art

Conventionally, endoscopes making it possible to observe an internal organ in a body cavity or an inside of an engine by inserting an elongated insertion portion into the body cavity or an engine plant have been widely used.

A distal end portion of the insertion portion of such an endoscope is provided with an optical unit having at least a part of an objective optical system. The optical unit has a moving barrel configured to hold an optical device, and the moving barrel is movable in an optical axis direction for a zoom function or a focus function.

As a technique for driving the moving barrel forward and backward, for example, a magnetic actuator for bifocal adjustment provided with an electromagnetic coil and a magnet as described in Japanese Patent Application Laid-Open Publication No. 2017-63845 is known.

SUMMARY OF THE INVENTION

An optical unit for endoscope according to an aspect of the present invention includes: a moving barrel which is a soft magnetic body, configured to hold an optical device; a fixed barrel which is a non-magnetic body, configured to movably hold the moving barrel on an inner circumferential face; a first yoke and a second yoke arranged on an outer surface of the fixed barrel, being separated from each other by a predetermined distance along an optical axis of the optical device; a coil formed being wound around the outer surface of the fixed barrel between the first yoke and the second yoke, with the optical axis as a central axis; a magnet arranged on a part of the coil in a circumferential direction on an outer circumferential side between the first yoke and the second yoke; and a magnetic body member with magnetism stronger than magnetism of the moving barrel, the magnetic body member being arranged on a part of the moving barrel in a circumferential direction, corresponding to the magnet; wherein as for each of the optical device, the coil, the magnet and the magnetic body member, at least one is provided.

An endoscope according to an aspect of the present invention includes an insertion portion with the optical unit for endoscope described above arranged on a distal end portion.

DETAILED DESCRIPTION OF THE PREFERRED EMBODIMENTS

Figure 1:
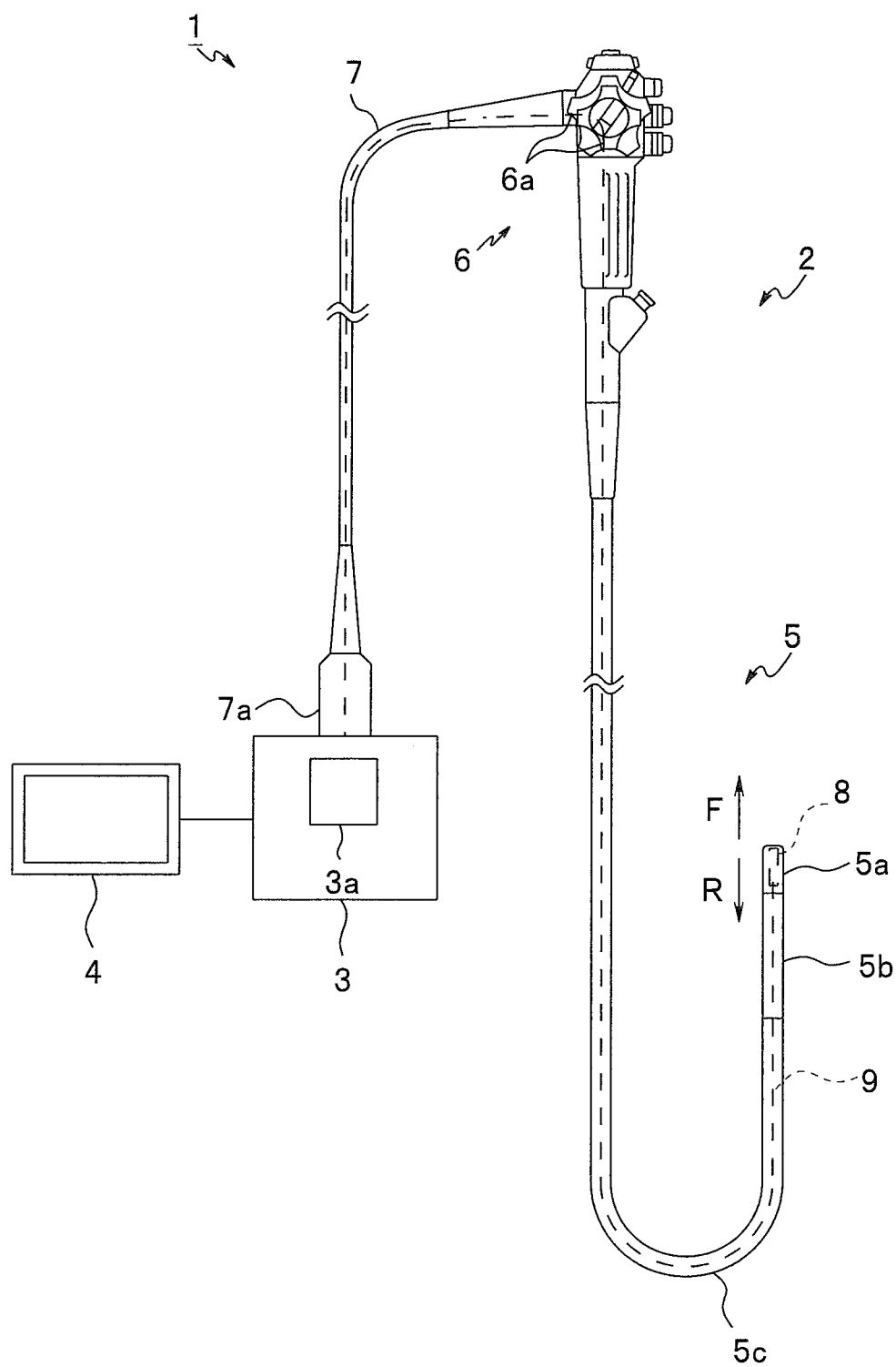
FIG. 1 is a diagram showing an example of an overall configuration of an endoscope system in a first embodiment of the present invention.

Embodiments of the present invention will be described with reference to drawings.

Note that, in each of the drawings used in description below, reduced scale may be caused to differ for each component to cause the component to be of a size recognizable on the drawing, and the present invention is not limited only to the number of components shown in the drawings, shapes of the components, a ratio of sizes of the components, relative positional relationship among the respective components.

First Embodiment

FIGS. 1 to 10 show a first embodiment of the present invention, and FIG. 1 is a diagram showing an example of an overall configuration of an endoscope system 1.

The endoscope system 1 of the present embodiment is provided with an endoscope 2, an external apparatus 3 and a display apparatus 4.

The endoscope 2 can be introduced into a subject such as a human body and is for optically observing an inside of the subject. Here, the subject into which the endoscope 2 is introduced is not limited to a human body but may be another living body or an artifact such as a machine or a building.

Though it is assumed that the endoscope 2 is an electronic endoscope configured to pick up an optical image of a subject in the present embodiment, the endoscope 2 is not limited to an electronic endoscope but may be an optical endoscope configured to transmit an optical image of a subject via a relay optical system or an optical fiber bundle.

The endoscope 2 is provided with an insertion portion 5 to be introduced into an inside of a subject, an operation portion 6 located at a proximal end of the insertion portion 5, and a universal cord 7 extending from a side portion of the operation portion 6.

The insertion portion 5 is configured of a distal end portion 5a disposed at a distal end, a bendable bending portion 5b disposed on a proximal end side of the distal end portion 5a, a flexible tube portion 5c having flexibility, which is disposed on the proximal end side of the bending portion 5b and is connected on a distal end side of the operation portion 6 which are connectedly provided.

Note that the endoscope 2 may be an endoscope in a form referred to as a so-called rigid endoscope, which is not provided with a portion having flexibility on the insertion portion 5.

The distal end portion 5a is provided with an image pickup apparatus 8 which is an image pickup unit in which an image pickup module is included. Therefore, an optical unit for endoscope 11 (see FIG. 2, FIG. 3 and the like) of the image pickup apparatus 8, which is described later, is also arranged on the distal end portion 5a of the insertion portion 5 of the endoscope 2.

The operation portion 6 is provided with an angle operation knob 6a for operating bending of the bending portion 5b.

A proximal end portion of the universal cord 7 is provided with an endoscope connector 7a to be electrically and optically connected with the external apparatus 3. The external apparatus 3 with which the endoscope connector 7a is to be connected is connected with the display apparatus 4 such as a monitor via a cable.

Inside the insertion portion 5, the operation portion 6 and the universal cord 7, from the image pickup apparatus 8 to the endoscope connector 7a described above, a composite cable 9 and a fiber bundle for illumination (not shown) are disposed.

The composite cable 9 is electrically connected with the image pickup apparatus 8 on a distal end side and is electrically connected with the endoscope connector 7a on a proximal end side. When the endoscope connector 7a and the external apparatus 3 are connected with each other, a power source is supplied, and a drive control signal is transmitted from the external apparatus 3 to the image pickup apparatus 8 via the composite cable 9, and an image pickup signal acquired by an image pickup device 12 (see FIG. 2) in the image pickup apparatus 8, which is described later, is transmitted to the external apparatus 3.

The fiber bundle for illumination is optically connected with the endoscope connector 7a on a proximal end side. When the endoscope connector 7a and the external apparatus 3 are connected with each other, the fiber bundle for illumination transmits illumination light from a light source portion (not shown) provided in the external apparatus 3. The illumination light transmitted by the fiber bundle for illumination is radiated toward a subject from the distal end portion 5a via an illumination window (not shown) as an illumination light emitting portion.

The external apparatus 3 is provided with an image processing portion 3a configured to perform image processing of an image pickup signal outputted from the image pickup apparatus 8 to generate an image signal. The image signal processed by the image processing portion 3a is outputted to the display apparatus 4, and an endoscopic image is displayed on the display apparatus 4.

Note that though the endoscope 2 is configured as a body separate from the external apparatus 3 and the display apparatus 4 here, for example, a configuration is also possible, regardless of the above, in which the endoscope 2 is provided with a part or all of functions of the external apparatus 3 (including the image processing portion 3a and the light source portion) and functions of the display apparatus 4. For example, an LED or the like has been used as a light source portion recently, so that downsizing is possible. Therefore, for example, a configuration is also possible in which the light source portion is disposed in the operation portion 6 or the distal end portion 5a of the endoscope 2.

Figure 2:
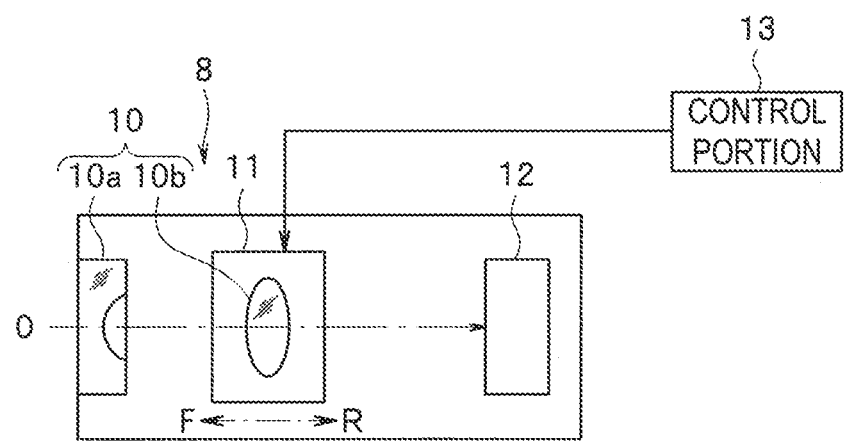
FIG. 2 is a diagram showing a configuration of an image pickup apparatus and a control portion configured to control the image pickup apparatus in the first embodiment.

FIG. 2 is a diagram showing a configuration of the image pickup apparatus 8 and a control portion 13 configured to control the image pickup apparatus 8.

As shown in FIG. 2, the image pickup apparatus 8 has an objective optical system 10 configured to form an optical image of a subject on the image pickup device 12, an optical unit for endoscope 11, which is a linear actuator for endoscope capable of moving at least one of optical devices constituting the objective optical system 10 forward (F) and rearward (R) along an optical axis O of the objective optical system 10, and the image pickup device 12 configured to perform photoelectrical conversion of the optical image formed by the objective optical system 10 to generate an image pickup signal.

In the example shown in FIG. 2, the objective optical system 10 is provided with lenses 10a and 10b as the optical devices (however, the optical devices are not limited to lenses). Here, each of the lenses 10a and 10b may be configured as a single lens or may be configured of a plurality of lenses.

The lens 10a is, for example, fixed to the image pickup apparatus 8, and the lens 10b is included in the optical unit for endoscope 11 and is movable along the optical axis O in the image pickup apparatus 8.

Movement of the lens 10b by the optical unit for endoscope 11 is controlled by the control portion 13.

Next, before specifically describing a configuration of the optical unit for endoscope 11 of the present embodiment, a basic configuration of the optical unit for endoscope 11 will be described with reference to FIGS. 3 and 4.

Figure 3:
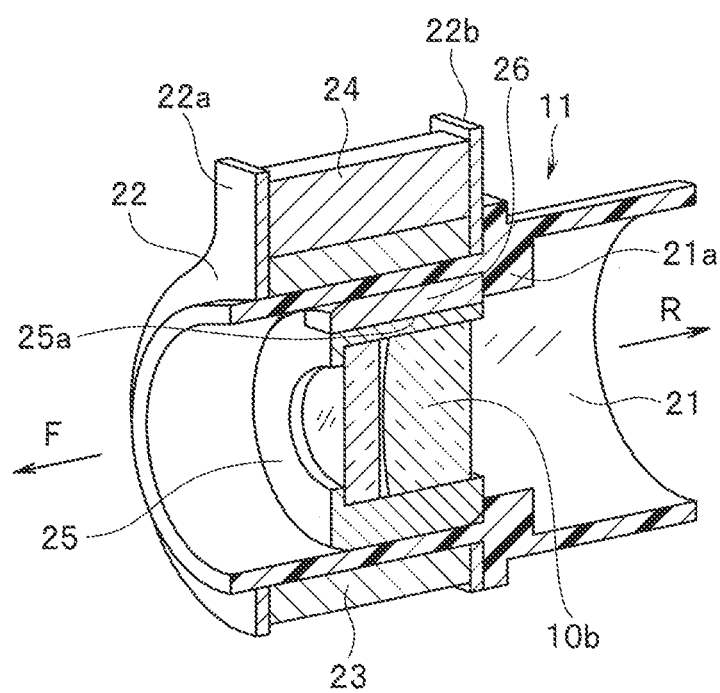
FIG. 3 is a sectional view in an optical axis direction showing a basic configuration of an optical unit for endoscope in the first embodiment.

First, FIG. 3 is a sectional view in a direction of the optical axis O showing the basic configuration of the optical unit for endoscope 11.

The optical unit for endoscope 11 is provided with a moving barrel 25 which is a soft magnetic body configured to hold the lens 10b which is an optical device, and a fixed barrel 21 which is a non-magnetic body configured to movably hold the moving barrel 25 on an inner circumferential face. Both of the fixed barrel 21 and the moving barrel 25 form cylindrical shapes, and the moving barrel 25 is slidable in the direction of the optical axis O on an inner circumferential side of the fixed barrel 21.

Yokes (collectively referred to as "the yokes," "the pair of yokes" or "the three yokes" 22) and a coil 23 constituting an electromagnet for moving the moving barrel 25 by magnetic force are disposed on an outer circumferential side of the fixed barrel 21.

The yokes 22 are for converging a magnetic flux generated from the coil 23 to strengthen magnetic force, and a pair of yokes 22 are provided corresponding to both poles of the electromagnet (the yokes 22 will be appropriately called such that the yoke on the F side is called a first yoke 22a and the other yoke on the R side is called a second yoke 22b, or the like). The pair of yokes 22 are magnetic bodies and formed to make a substantially doughnut-disk shape (or another shape such as a shape having an inwardly projecting portion in a doughnut-disk shape (see, for example, FIG. 15, FIG. 16 and the like)), and the pair of yokes 22 are arranged on an outer surface (an outer circumferential face) of the fixed barrel 21 with a predetermined distance between the pair of yokes 22 along the optical axis O.

The coil 23 is configured of a metal wire having electrical conductivity, for example, a copper wire, and is formed by being wound around the outer surface (the outer circumferential face) of the fixed barrel 21 between the first yoke 22a and the second yoke 22b, with the optical axis O of the objective optical system 10 as a central axis.

Between the first yoke 22a and the second yoke 22b, a permanent magnet (hereinafter, referred to simply as "a magnet") 24 is arranged as a fixed barrel magnet on a part of the coil 23 in a circumferential direction on an outer circumferential side (a particular part of the coil 23 in the circumferential direction on the outer circumferential side). In the example shown in FIG. 3, the magnet 24 forms a rectangular rod shape (a rod shape with a rectangular section, that is, a rectangular parallelepiped shape) in the direction of the optical axis O, and only parts of the pair of yokes 22 where the magnet 24 is arranged project in an outer diameter direction and support both ends of the magnet 24 in the direction of the optical axis O.

Further, on a part of the moving barrel 25 in a circumferential direction, a magnetic body portion (a magnetic body member) with magnetism stronger than magnetism of the moving barrel 25 is arranged. In the example shown in FIG. 3, the magnetic body portion is a magnet 26 (a moving barrel magnet) forming a rectangular rod shape (a rectangular parallelepiped shape) in the direction of the optical axis O and is disposed being buried in a recess portion 25a formed on a particular part of the moving barrel 25 in the circumferential direction on an outer circumferential side (a position corresponding to the magnet 24).

Here, strength of magnetism of the magnet 24 constituting the magnetic actuator is set to be, for example, more than the strength of magnetic force of the magnet 26 arranged on the moving barrel 25. Further, since the moving barrel 25 is formed of a soft magnetic body, the magnetism of the magnet 26, which is a magnetic body portion, is stronger than the magnetism of the moving barrel 25.

Thus, the optical unit for endoscope 11 is basically configured being provided with at least one optical device such as a lens, at least one coil 23, at least one magnet 24 and at least one magnetic body portion such as the magnet 26 (an example in which two or more coils 23 and magnets 24 and 26 will be described later with reference to FIG. 5 and the like).

Note that a movement position of the moving barrel 25 in forward (F) and rearward (R) directions in the fixed barrel 21 is restricted by an appropriate stopper mechanism (such as an engaging portion (including a recess portion and a flange)). In the example shown in FIG. 3, the movement position in the rearward (R) direction is restricted by an inner flange 21a projectingly provided on the inner circumferential side of the fixed barrel 21 (as for the forward (F) direction, the stopper mechanism (a recess portion or the like) is not shown). However, regardless of the above, a recess portion or the like may be used to restrict the movement position in the rearward (R) direction.

Figure 4:
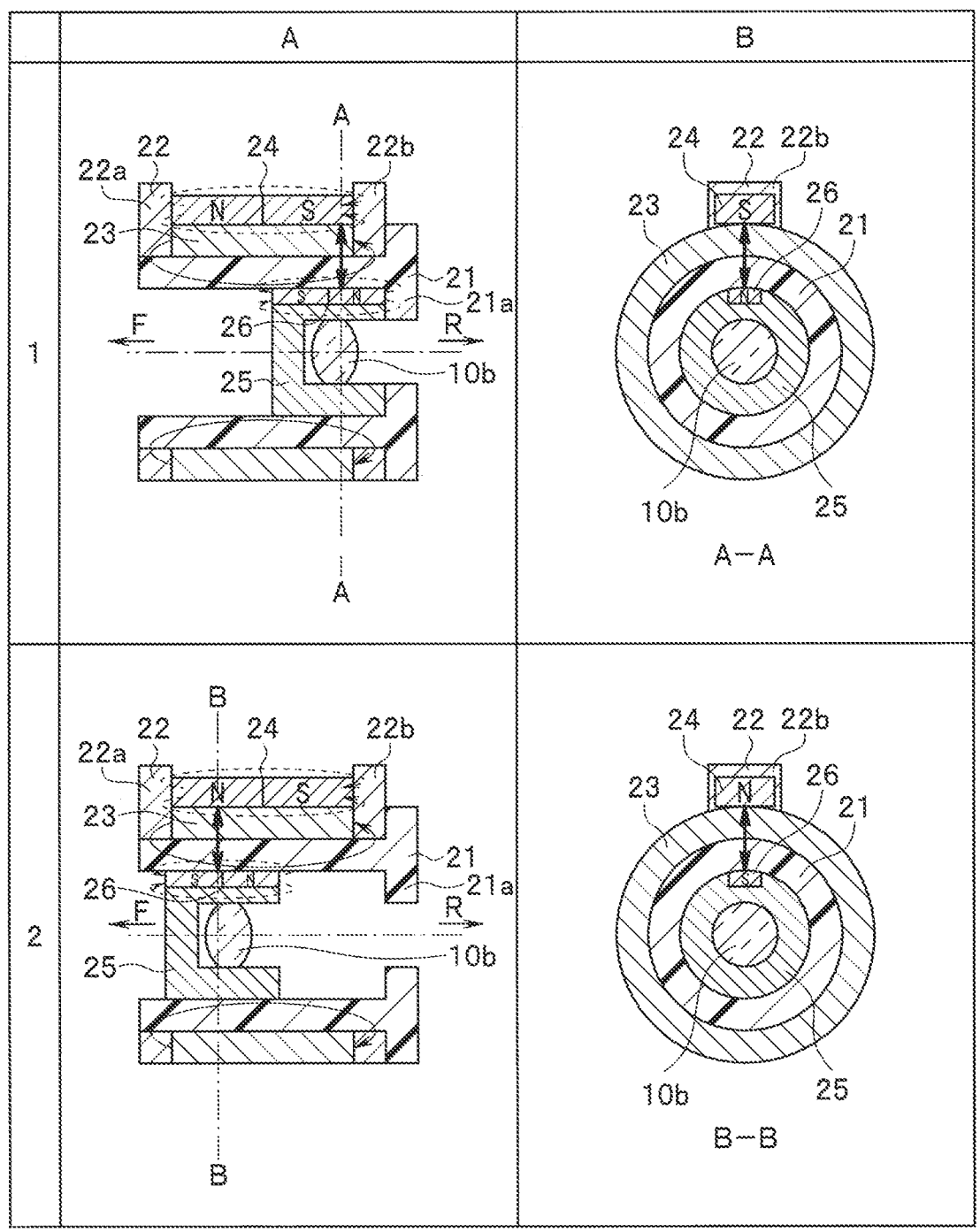
FIG. 4 is a diagram chart showing states of the optical unit for endoscope with the basic configuration at two rest positions in the first embodiment.

FIG. 4 is a diagram chart showing states of the optical unit for endoscope 11 with the basic configuration at two rest positions.

By supplying a current from the control portion 13 to the coil 23, such a magnetic circuit that a magnetic field generated from the coil 23 passes through one of the pair of yokes 22, the fixed barrel 21, the moving barrel 25, the fixed barrel 21 and the other of the pair of yokes 22 and returns to the coil 23 is formed (see curved solid-line arrows (note that the curved arrows do not pass the moving barrel 25 because each of the curved arrows indicates one of magnetic force lines, but some of the plurality of magnetic force lines starting from and ending at the coil 23 pass through the moving barrel 25)). At this time, by causing a direction of the current supplied to the coil 23 to change to a forward or reverse direction, it is possible to cause a direction of the magnetic field passing through the moving barrel 25 to change to the forward (F) or rearward (R) direction.

In the example shown in FIG. 4, the magnet 24 is magnetized so that the F side is the N-pole, and the R side is the S-pole, and the magnet 26 is magnetized so that the F side is the S-pole, and the R side is the N-pole. Magnetic force lines caused from the magnets 24 and 26 are indicated by curved dotted-line arrows in FIG. 4.

However, since the yokes 22 are provided, a main passage route of the magnetic force lines generated from the magnet 24 is a route passing through the yokes 22. In other words, the magnetic force lines starting from the N-pole of the magnet 24 concentratedly enter the yoke 22a that is in contact with the N-pole of the magnet 24, pass through the fixed barrel 21, which is a non-magnetic body, from the yoke 22a and reach the F side of the moving barrel 25 which is a soft magnetic body. At this time, the F side of the moving barrel 25 is magnetized to be the S-pole, and the R side is magnetized to be the N-pole. After that, the magnetic force lines start from the R side of the moving barrel 25, pass through the fixed barrel 21, which is a non-magnetic body, concentratedly enter the yoke 22b that is in contact with the S-pole of the magnet 24, enter the S-pole of the magnet 24 from the yoke 22b, the S-pole being an end point.

In fields 1A and 1B (the field 1B shows an A-A section in the field 1A), a state is shown in which the moving barrel 25 is in contact with the inner flange 21a and at a rest position in the R direction. At this time, as indicated by solid-line bi-directional arrows, the S-pole of the magnet 24 (more accurately, an inner-circumferential-side end face of the yoke 22b that is in contact with the S-pole of the magnet 24 as described above; the same applies hereinafter) and the N-pole of the magnet 26 exert magnetic attraction on each other and restrict movement from the rest position. Note that though the N-pole (more accurately, an inner-circumferential-side end face of the yoke 22a that is in contact with the N-pole of the magnet 24 as described above; the same applies hereinafter) of the magnet 24 and the S-pole of the magnet 26 also exert magnetic attraction on each other, the magnetic attraction acting between the S-pole of the magnet 24 and the N-pole of the magnet 26 is larger than the magnetic attraction acting between the N-pole of the magnet 24 and the S-pole of the magnet 26 because a distance between the N-pole of the magnet 24 and the S-pole of the magnet 26 is larger than a distance between the S-pole of the magnet 24 and the N-pole of the magnet 26, and, therefore, the rest position shown in the 1A filed of FIG. 4 is maintained.

In fields 2A and 2B (the field 2B shows a B-B section in the field 2A), a state is shown in which the moving barrel 25 is at a rest position in the F direction by the stopper mechanism not shown. At this time, as indicated by solid-line bi-directional arrows, the N-pole of the magnet 24 and the S-pole of the magnet 26 exert magnetic attraction on each other and restrict movement from the rest position. Similarly to the above description, the magnetic attraction acting between the N-pole of the magnet 24 and the S-pole of the magnet 26 is larger than the magnetic attraction acting between the S-pole of the magnet 24 and the N-pole of the magnet 26.

Thus, the optical unit for endoscope 11 is a magnetic linear actuator for endoscope having two rest positions in the direction of the optical axis O. If, for example, a focus lens is used as the lens 10b, the objective optical system 10 capable of switching between two focus positions can be configured.

A rotation position of the moving barrel 25 around the optical axis O at the rest position shown in the fields 1A and 1B and a rotation position of the moving barrel 25 around the optical axis O at the rest position shown in the fields 2A and 2B are the same. Therefore, it is possible to, by the rotation positions of the moving barrel 25 (therefore, of the lens 10b) around the optical axis O and inclinations relative to the optical axis O being the same at the two rest positions, prevent degradation of optical performance due to misalignment of the optical device. More specifically, it is possible to prevent displacement (eccentricity) of a center of the lens 10b from the optical axis O and prevent inclination of the lens 10b relative to the optical axis O at the two rest positions.

Next, a more specific configuration and operation of the optical unit for endoscope 11 of the present embodiment will be described with reference to FIGS. 5 to 10.

Figure 5:
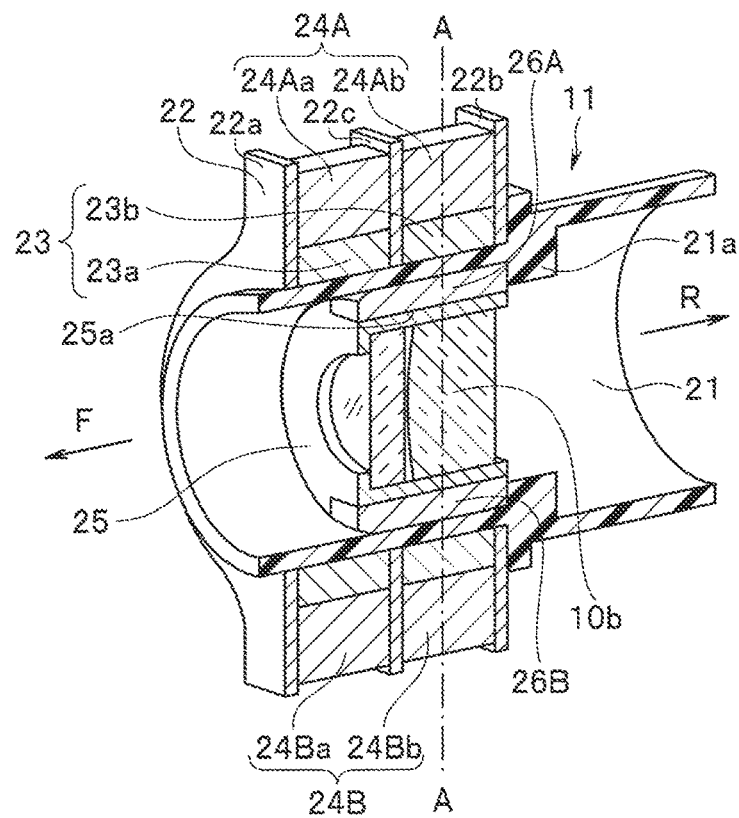
FIG. 5 is a sectional view in the optical axis direction showing a configuration example of the optical unit for endoscope in the first embodiment.
Figure 6:
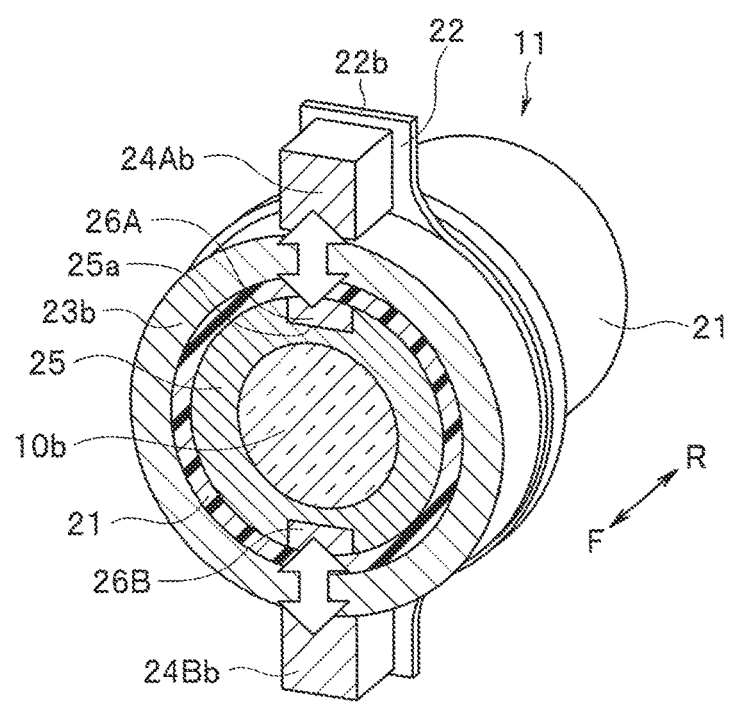
FIG. 6 is a diagram showing an A-A section of the optical unit for endoscope in FIG. 5 in the first embodiment.

FIG. 5 is a sectional view in the direction of the optical axis O showing a configuration example of the optical unit for endoscope 11, and FIG. 6 is a diagram showing an A-A section of the optical unit for endoscope 11 in FIG. 5.

The optical unit for endoscope 11 shown in FIG. 5 is different from the basic configuration described with reference to FIG. 3 in the following points.

The magnet 24 includes a magnet 24A which is a first magnet arranged at a first position in the circumferential direction on the outer circumferential side of the coil 23, and a magnet 24B which is a second magnet arranged at a second position different from the first position in the circumferential direction on the outer circumferential side of the coil 23. In the example shown in FIG. 5, the first and second positions are facing positions in the circumferential direction, that is, positions that are different by 180° around the optical axis O. On the other hand, the magnets 24A and 24B are at the same position in the direction of the optical axis O.

The magnet 26 which is a magnetic body portion includes a magnet 26A which is a first magnetic body portion (a first magnetic body member) arranged at a first position in the circumferential direction of the moving barrel 25 corresponding to the magnet 24A, and a magnet 26B which is a second magnetic body portion (a second magnetic body member) arranged at a second position different from the first position in the circumferential direction of the moving barrel 25 corresponding to the magnet 24B. More specifically, since the magnets 24A and 24B of the fixed barrel 21 are arranged at positions that are different by 180° around the optical axis O on the outer circumferential side of the coil 23, the magnets 26A and 26B of the moving barrel 25 corresponding to the magnets 24A and 24B, respectively, are also arranged at positions different by 180° around the optical axis O. The magnets 26A and 26B are at the same position in the direction of the optical axis O.

Thus, at least one magnet 24A which is a first magnet, at least one magnet 24B which is a second magnet, at least one magnet 26A which is the first magnetic body portion and at least one magnet 26B which is the second magnetic body portion are provided.

More specifically, the coil 23 includes a first coil 23a (the F side) and a second coil 23b (the R side) arranged at different positions along the optical axis O between the first yoke 22a and the second yoke 22b. Between the first coil 23a on the F side and the second coil 23b on the R side, that is, between the first yoke 22a and the second yoke 22b, a third yoke 22c is disposed. Note that, similarly to the above description, each of the three yokes 22 projects in the outer diameter direction at the positions where the magnets 24A and 24B are provided, respectively.

The magnet 24A which is the first magnet includes a magnet 24Aa which is a magnet (a first magnet (1)) arranged on an outer circumferential side of the first coil 23a and a magnet 24Ab which is a magnet (a first magnet (2)) arranged on an outer circumferential side of the second coil 23b.

The magnet 24B which is a second magnet includes a magnet 24Ba which is a magnet (a second magnet (1)) arranged on the outer circumferential side of the first coil 23a and a magnet 24Bb which is a magnet (a second magnet (2)) arranged on the outer circumferential side of the second coil 23b.

Thus, the optical unit for endoscope 11 is provided with two electromagnets at different positions in the direction of the optical axis O; the first electromagnet on the F side is provided with the coil 23a, the first yoke 22a and the third yoke 22c; and the second electromagnet on the R side is provided with the coil 23b, the second yoke 22b and the third yoke 22c (therefore, the third yoke 22c is used by both of the first and second electromagnets).

Here, since the first and second electromagnets share the one third yoke 22c, it is possible to reduce the number of parts to simplify the configuration and reduce weight of the optical unit for endoscope 11.

However, instead of the configuration in which the one third yoke 22c is shared, a configuration may be adopted in which each of the first and second electromagnets is individually provided with the third yoke 22c. In this case, since it is only required to assemble each of the first and second electromagnets that are individually configured to the fixed barrel 21, assemblability of the optical unit for endoscope 11 can be improved. Furthermore, since each of the first and second electromagnets is provided with a dedicated third yoke 22c, the number of magnetic force lines increases, and it becomes possible to hold the moving barrel 25 at a rest position with a higher holding power.

The two electromagnets are mutually independently controlled by the control portion 13, and a direction (a forward/reverse direction) and a current value of a current supplied from the control portion 13 to the coil 23a and a direction (a forward/reverse direction) and a current value of a current supplied from the control portion 13 to the coil 23b are mutually independently controlled.

The F-side rest position of the moving barrel 25 attracted by the first electromagnet is maintained by the magnets 24Aa and 24Ba when a current is not flowing through the coils 23a and 23b, and the R-side rest position of the moving barrel 25 attracted by the second electromagnet is maintained by the magnets 24Ab and 24Bb when a current is not flowing through the coils 23a and 23b.

Figure 7:
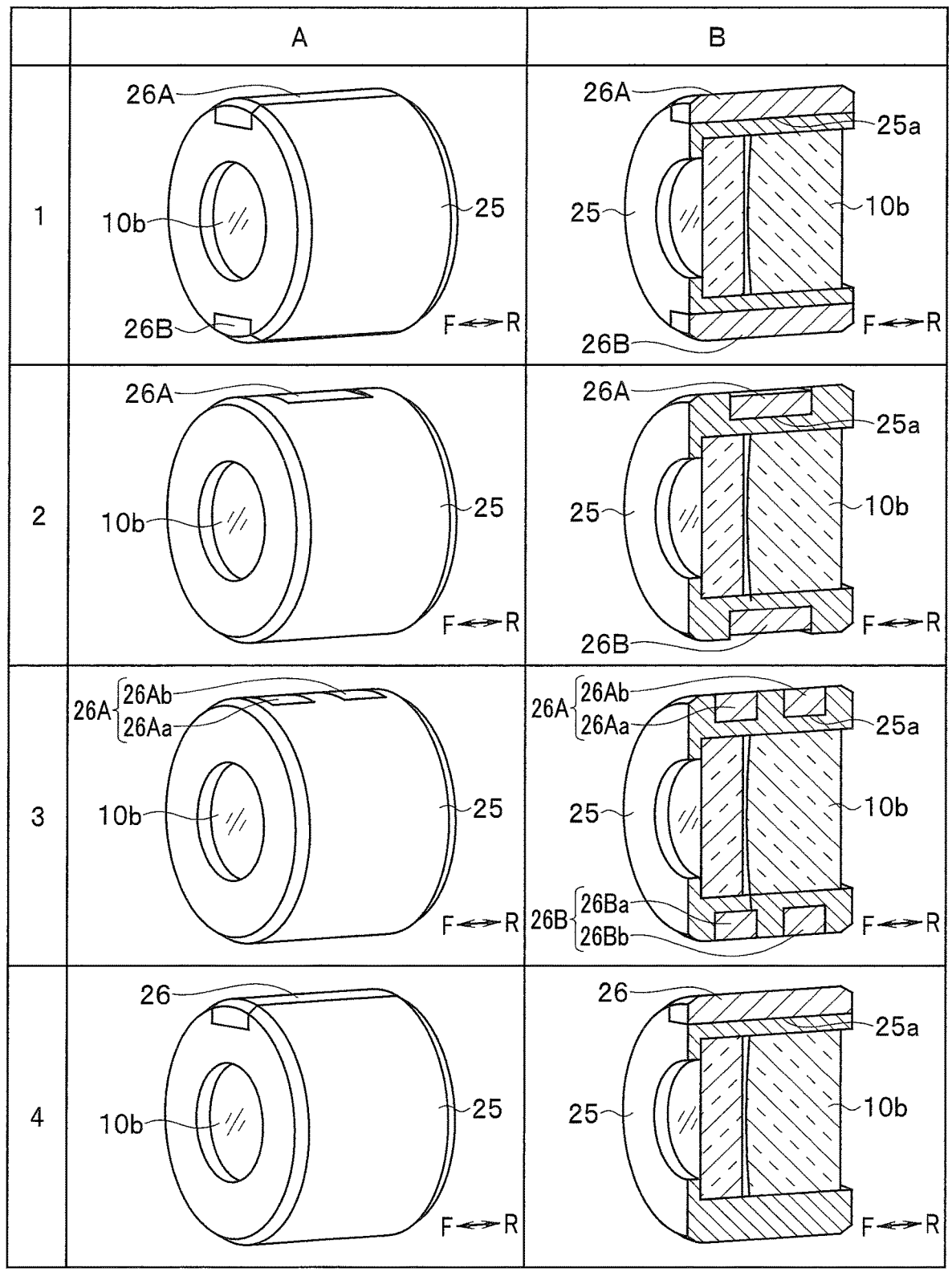
FIG. 7 is a diagram chart showing configuration examples of a magnetic body portion (magnetic body portions) provided on a moving barrel in the first embodiment.

FIG. 7 is a diagram chart showing configuration examples of a magnetic body portion (magnetic body portions) provided on the moving barrel 25. In FIG. 7, columns A and B show perspective views and sectional views in the direction of the optical axis O, respectively.

The magnets 26A and 26B which are magnetic body portions shown in fields 1A and 1B are elongatedly provided in the direction of the optical axis O from an F-side end face to an R-side end face of the moving barrel 25. Such a configuration can be achieved by forming two grooves in the direction of the optical axis O on an outer circumferential face of the moving barrel 25 as recess portions 25a, and fixing the magnets 26A and 26B in the two formed grooves using adhesive or the like. The grooves in the direction of the optical axis O has an advantage of being relatively easily formed.

The magnets 26A and 26B shown in the fields 2A and 2B are configured by forming rectangular holes as the recess portions 25a in the middle in the direction of the optical axis O on the outer circumferential face of the moving barrel 25, and fitting the magnets 26A and 26B into the formed rectangular holes, respectively, and fixing the magnets 26A and 26B with adhesive or the like. Furthermore, the magnets 26A and 26B shown in the fields 2A and 2B are configured, for example, such that surfaces are flat, and are configured being recessed from the outer circumferential face of the moving barrel 25 (that is, a configuration of being arranged being buried below the outer circumferential face of the moving barrel 25). Thereby, it is possible to avoid the magnets 26A and 26B from coming into contact with the inner circumferential face of the fixed barrel 21 when the moving barrel 25 moves, and it is possible to effectively prevent wear and damage of the magnets 26A and 26B configured of ceramic or the like.

The magnets 26A and 26B shown in fields 3A and 3B are configured of two magnets 26Aa and 26Ab and two magnets 26Ba and 26Bb in the direction of the optical axis O, respectively. Thus, the magnetic body portions shown in the fields 3A and 3B include the magnets 26Aa and 26Ba which are distal-end-side magnetic body portions (distal-end-side magnetic body members) and the magnets 26Ab and 26Bb which are proximal-end-side magnetic body portions (proximal-end-side magnetic body members), which are arranged at different positions along the optical axis O on the moving barrel 25. Each of the magnets 26Aa, 26Ab, 26Ba and 26Bb is also configured by forming a rectangular hole on the outer circumferential face of the moving barrel 25, fitting the magnet into the formed rectangular hole and fixing the magnet with adhesive or the like. Note that a length of the magnets 26 is not limited to a particular length as seen when the rows 1 to 3 are compared.

Furthermore, the moving barrel 25 provided with only one magnet 26 is shown in fields 4A and 4B. The magnet 26 is almost similar to the magnet 26 with the basic configuration shown in FIG. 3 and is elongatedly provided in the direction of the optical axis O from the F-side end face to the R-side end face of the moving barrel 25. Note that, in the case of using the moving barrel 25 with the configuration shown in the fields 4A and 4B, the magnet 24B and the projections of the yokes 22 in the outer diameter direction shown in FIGS. 5 and 6 are unnecessary.

Therefore, positioning of the moving barrel 25 may be performed either by a pair of magnets in a radial direction or by offsetting on one side in the radial direction.

As the recess portion 25a for attaching the magnet 26 to the moving barrel 25, a groove (grooves) is formed in the examples shown in the rows 1 and 4 among the rows shown in FIG. 7, and holes (for example, rectangular holes) are formed in the examples shown in the rows 2 and 3 in FIG. 7.

Note that as shown in the rows 1 to 3 in FIG. 7, in the case of arranging a plurality of magnets 26 on the moving barrel 25, it is desirable to unify positions where the respective magnets 26 are arranged, shapes of the respective magnets 26, lengths of the respective magnets 26 and the like. Thereby, it becomes possible to more appropriately restrict inclination relative to the optical axis O caused when the moving barrel 25 moves.

Figure 8:
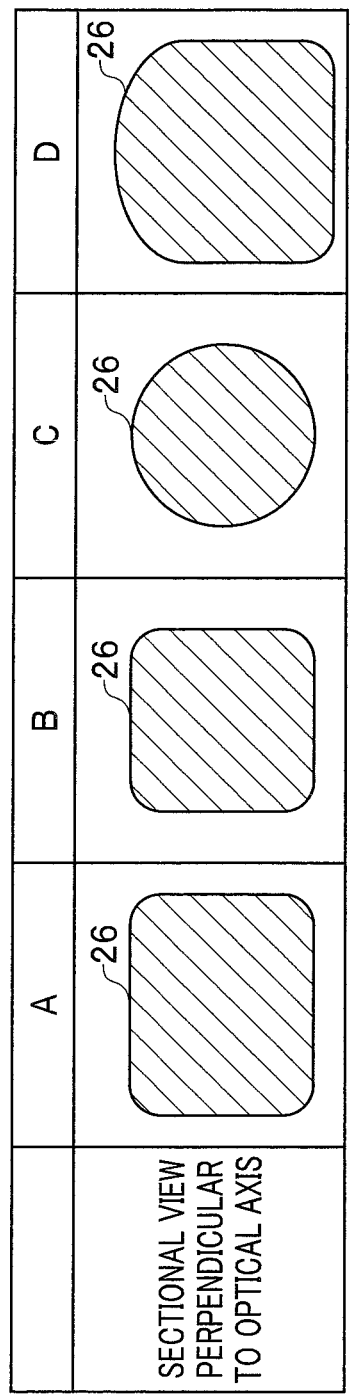
FIG. 8 is a diagram chart showing examples of a shape of a section of the magnetic body portion provided on the moving barrel, the section being perpendicular to the optical axis, in the first embodiment.

FIG. 8 is a diagram chart showing examples of a shape of a section of the magnet 26, which is a magnetic body portion provided on the moving barrel 25, the section being perpendicular to the optical axis O (the magnet 26 includes the magnets 26A and 26B as described above; the same applies hereinafter). In FIG. 8, a lower side indicates an inner diameter side (the optical axis O side), and an upper side indicates an outer diameter side (the outer circumferential face side of the moving barrel 25).

A field A shows a section in a rectangular shape with rounded corners; a field B shows a section in a square shape with rounded corners; a field C shows a section in a circular shape; and a field D shows a section the inner diameter side of which forms a rectangular shape with rounded corners and the outer diameter side of which forms an arc shape along the outer circumferential surface of the moving barrel 25.

As for the magnet 26 in each of the fields A, B and D among the above fields, a groove or a hole with a rectangular-shaped section is formed on the outer circumferential face of the moving barrel 25, and the magnet 26 is fitted into the groove or the hole. As for the magnet 26 in the field C, a groove or a hole with a circular-shaped section is formed on the outer circumferential face of the moving barrel 25, and the magnet 26 is fitted into the groove or the hole.

Thus, outer side faces of the magnets 26 in the fields A and B are on an inner diameter side of the outer circumferential face of the moving barrel 25, and it is possible to avoid the outer side faces from coming into contact with the inner circumferential face of the fixed barrel 21. The magnets 26 in the fields C and D can also be configured so that outside faces (or parts of the outside faces projecting most) correspond to the outer circumferential face of the moving barrel 25. For example, if the outside face of the magnet 26 in the field D is caused to correspond to the outer circumferential face of the moving barrel 25, it is possible to keep slidability constant even in the case of a different position in the circumferential direction. However, a configuration is also possible in which a contact of the magnet 26 with the inner circumferential face of the fixed barrel 21 is prevented by forming the recess portion 25a (a groove or a hole) in which the magnet 26 in the field C or D is to be attached deeper.

Note that though description has been made on the assumption that FIG. 8 shows shapes of the section of the magnet 26 perpendicular to the optical axis O, the shapes may be, regardless of the above, shapes when the magnet 26 is seen from an outer diameter direction or an inner diameter direction.

Therefore, the magnet 26 may be in any three-dimensional shape such as a rectangular parallelepiped shape, a cubic shape, a rod shape, a cylindrical shape, a spherical shape or a semi-cylindrical shape. Since it is possible to flexibly adopt various kinds of shapes (or sizes and lengths) for the magnet 26, there is an advantage that, by selecting a shape in consideration of processability, the magnet 26 is hardly influenced by the processability.

Figure 9:
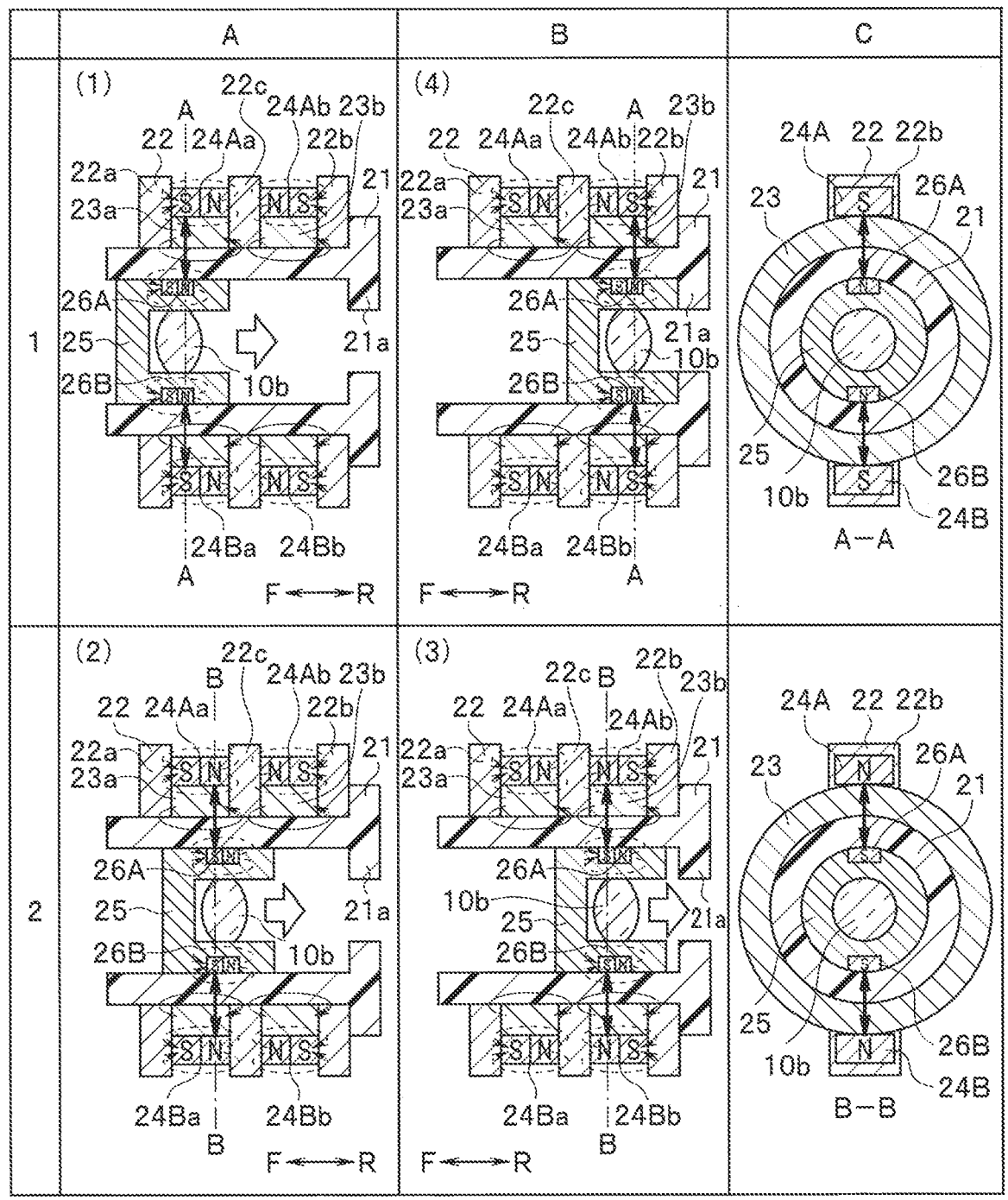
FIG. 9 is a diagram chart showing operation of the optical unit for endoscope in the first embodiment.

FIG. 9 is a diagram chart showing operation of the optical unit for endoscope 11. In FIG. 9, columns A and B show sectional views of the optical unit for endoscope 11 in the direction of the optical axis O, and a column C shows diagrams when an A-A section and a B-B section of the optical unit for endoscope 11 perpendicular to the optical axis O are seen in an R direction.

All of the magnets 24Aa and 24Ab, and the magnets 24Ba and 24Bb are provided with magnetic poles in the direction of the optical axis O. In the example shown in FIG. 9, the N-poles of the magnet 24Aa and the magnet 24Ab are arranged to face each other in the direction of the optical axis O, and the N-poles of the magnet 24Ba and the magnet 24Bb are arranged to face each other in the direction of the optical axis O.

Further, in the example shown in FIG. 9, the magnets 26A and 26B are provided with magnetic poles in the direction of the optical axis O (therefore, magnetic poles in directions that are parallel to and the same as, or parallel to and opposite to directions of magnetic poles of the magnets 24Aa, 24Ab, 24Ba and 24Bb) and are arranged so that the F side is the S-pole, and the R side is the N-pole.

However, arrangement of each of the magnets 24Aa, 24Ab, 24Ba, 24Bb, 26A and 26B is not limited to the above. The magnets 24Aa, 24Ab, 24Ba, 24Bb, 26A and 26B may be arranged so that all the polarities are reversed.

A field 1A(1) shows a state in which the moving barrel 25 is at a rest position on the F side. At this time, as indicated by solid-line bi-directional arrows in fields 1A and 1C, the S-pole of the magnet 24Aa and the N-pole of the magnet 26A exert magnetic attraction on each other, and the S-pole of the magnet 24Ba and the N-pole of the magnet 26B exert magnetic attraction on each other. Thereby, movement from the rest position is restricted.

Similarly to the above description made with reference to FIG. 4, since magnetic attraction acting between the S-pole of the magnet 24Aa and the N-pole of the magnet 26A is larger than magnetic attraction acting between the N-pole of the magnet 24Aa and the S-pole of the magnet 26A, and magnetic attraction acting between the S-pole of the magnet 24Ba and the N-pole of the magnet 26B is larger than magnetic attraction acting between the N-pole of the magnet 24Ba and the S-pole of the magnet 26B at this time due to difference between distances, the rest position shown in the field 1A of FIG. 9 is maintained when a current is not flowing through the coils 23a and 23b.

When a current is applied to the coils 23a and 23b, magnetic fields are generated from the coils 23a and 23b. At this time, the current is applied to the coils 23a and 23b so that the magnetic fields in directions indicated by curved solid-line arrows are generated in each of fields 1A, 1B, 2A and 2B of FIG. 9.

More specifically, the magnetic field generated from the coil 23a acts to weaken magnetic fields of the magnets 24Aa and 24Ba because the magnetic field generated from the coil 23a is in a direction opposite to a direction of the magnetic fields of the magnets 24Aa and 24Ba, and the magnetic field generated from the coil 23b acts to strengthen magnetic fields of the magnets 24Ab and 24Bb because the magnetic field generated from the coil 23b is in the same direction as the direction of the magnetic fields of the magnets 24Ab and 24Bb.

Thus, a magnetic field obtained by combining the magnetic field of the coil 23b and the magnetic fields of the magnets 24Ab and 24Bb is stronger than a magnetic field obtained by combining the magnetic field of the coil 23a and the magnetic fields of the magnets 24Aa and 24Ba, and the moving barrel 25 formed by a soft magnetic body is attracted to the coil 23b and the magnets 24Ab and 24Bb and moves in the R direction.

Note that though the direction of the magnetic fields of the coils 23a and 23b is opposite to a direction of the magnets 26A and 26B of the moving barrel 25, the moving barrel 25 can smoothly move because, as described above, magnetic force of the magnets 26A and 26B is smaller than magnetic force of the magnets 24Aa, 24Ba, 24Ab and 24Bb constituting the magnetic actuator, and a magnitude of the magnetic fields generated from the coils 23a and 23b is sufficient.

The field 2A(2) shows a state at the time when the moving barrel 25 has moved a little in the R direction from the rest state in the field 1A(1). At this time, as indicated by solid-line bi-directional arrows in fields 2A and 2C, the N-pole of the magnet 24Aa and the S-pole of the magnet 26A exert magnetic attraction on each other, and the N-pole of the magnet 24Ba and the S-pole of the magnet 26B exert magnetic attraction on each other. Thereby, the moving barrel 25 is restricted from rotating around the optical axis O and is prevented from inclining relative to the optical axis O.

The field 2B(3) shows a state at the time when the moving barrel 25 has further moved a little in the R direction from the state in the field 2A(2). At this time, as indicated by solid-line bi-directional arrows in the fields 2B and 2C, the N-pole of the magnet 24Ab and the S-pole of the magnet 26A exert magnetic attraction on each other, and the N-pole of the magnet 24Bb and the S-pole of the magnet 26B exert magnetic attraction on each other. Thereby, the moving barrel 25 is restricted from rotating around the optical axis O and is prevented from inclining relative to the optical axis O. Thus, as shown in (2) and (3), since inclination of the moving barrel 25 at the time of moving can be prevented, it is possible to preferably restrict sliding failure relative to the inner circumferential face of the fixed barrel 21 caused when the moving barrel 25 inclines.

The field 1B(4) shows a state at the time when the moving barrel 25 has further moved in the R direction from the state in the field 2B(3) and reached a rest position on the R side. At this time, as indicated by solid-line bi-directional arrows in the fields 1B and 1C, the S-pole of the magnet 24Ab and the N-pole of the magnet 26A exert magnetic attraction on each other, and the S-pole of the magnet 24Bb and the N-pole of the magnet 26B exert magnetic attraction on each other. Thereby, movement from the rest position is prevented. Thereby, similarly to the above description, the rest position shown in the field 1B of FIG. 9 is maintained when a current is not flowing through the coils 23a and 23b.

Since rotation positions of the moving barrel 25 around the optical axis O are the same in the state of (1) and the state of (4), it is possible to, by the rotation positions of the moving barrel 25 (therefore, of the lens 10) around the optical axis O and inclinations relative to the optical axis O being the same at the two rest positions, restrict eccentricity caused by the center of the lens 10b being displaced from the optical axis O and prevent degradation of the optical performance due to misalignment of the optical device.

Movement of the moving barrel 25 from the rest position on the R side shown in the field 1B(4) to the rest position on the F side shown in the field 1A(1) is performed by applying a current in a direction opposite to the direction described above to the coils 23a and 23b to generate magnetic fields in a direction opposite to the direction of the curved solid-line arrows in the respective fields 1A, 1B, 2A and 2B of FIG. 9.

More specifically, the magnetic field generated from the coil 23a at this time acts to strengthen the magnetic fields of the magnets 24Aa and 24Ba because the magnetic field generated from the coil 23a is in the same direction as the direction of the magnetic fields of the magnets 24Aa and 24Ba, and the magnetic field generated from the coil 23b acts to weaken the magnetic fields of the magnets 24Ab and 24Bb because the magnetic field generated from the coil 23b is in a direction opposite to the direction of the magnetic fields of the magnets 24Ab and 24Bb.

Thereby, a magnetic field obtained by combining the magnetic field of the coil 23a and the magnetic fields of the magnets 24Aa and 24Ba is stronger than a magnetic field obtained by combining the magnetic field of the coil 23b and the magnetic fields of the magnets 24Ab and 24Bb, and the moving barrel 25 formed by a soft magnetic body is attracted to the coil 23a and the magnets 24Aa and 24Ba and moves in the F direction. Similarly to the above description, at the time of the movement, rotation of the moving barrel 25 around the optical axis O and inclination of the moving barrel 25 relative to the optical axis O are prevented by the action of the magnets 24A and 26A and the action of the magnets 24B and 26B.

Note that though driving force is somewhat low at the time of moving in the F direction in comparison with the time of moving in the R direction because the direction of the magnetic fields generated from the coils 23a and 23b is the same as a direction of magnetic fields of the magnets 26A and 26B of the moving barrel 25, the moving barrel 25 can smoothly move because the magnitude of the magnetic fields generated from the coils 23a and 23b is sufficient.

Similarly to the above description, since the rotation positions of the moving barrel 25 around the optical axis O are the same in the state of (4) and the state of (1), it is possible to prevent misalignment of the optical device at the two rest positions and prevent degradation of the optical performance.

Figure 10:
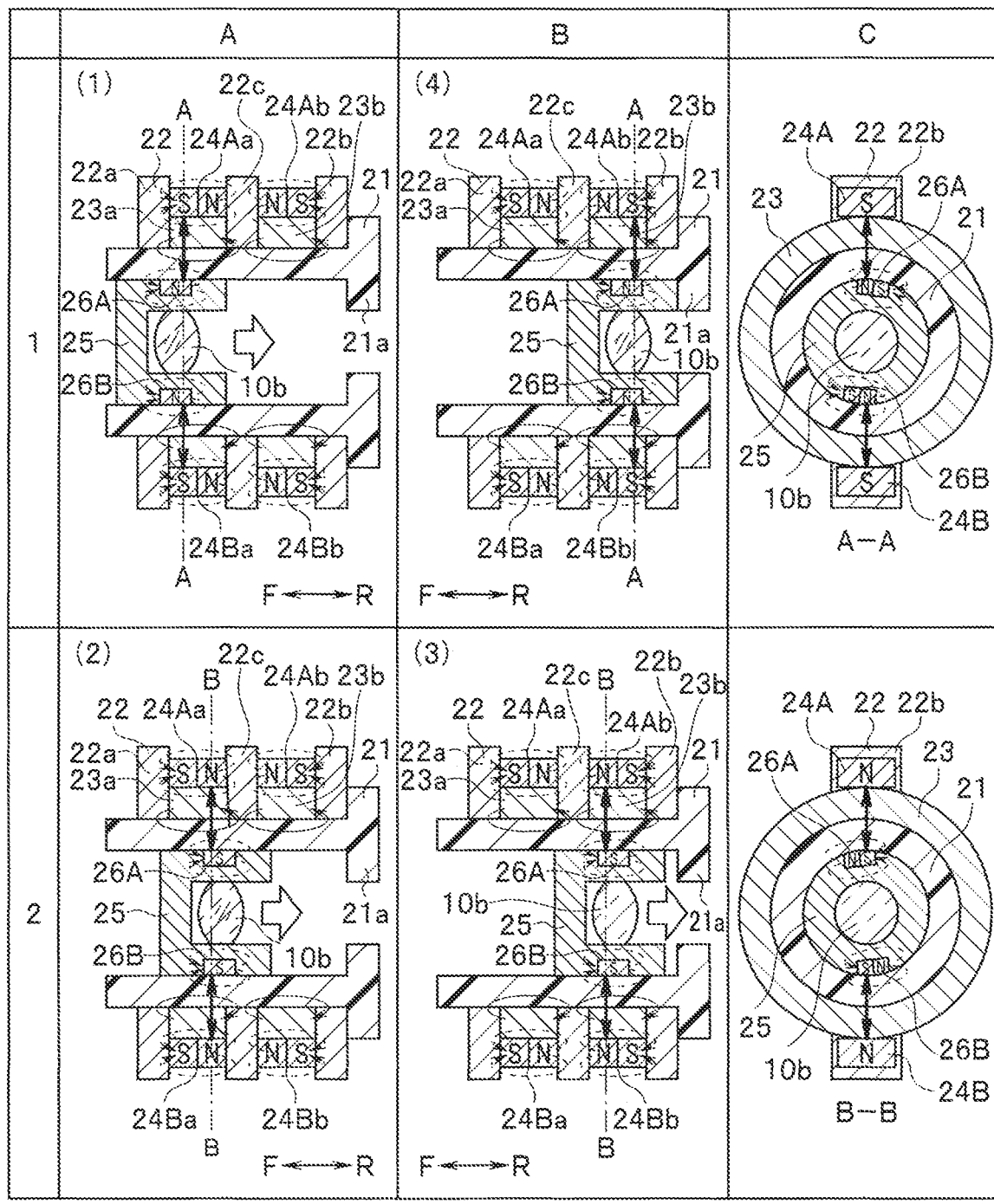
FIG. 10 is a diagram chart showing operation of a modification of the optical unit for endoscope in the first embodiment.

FIG. 10 is a diagram chart showing operation of a modification of the optical unit for endoscope 11. In FIG. 10, columns A and B show sectional views of the optical unit for endoscope 11 in the direction of the optical axis O, and a column C shows diagrams when an A-A section and a B-B section of the optical unit for endoscope 11 perpendicular to the optical axis O are seen in an R direction.

In the example shown in FIG. 10, though arrangement of the magnets 24Aa, 24Ab, 24Ba and 24Bb is similar to the arrangement in FIG. 9, arrangement of the magnets 26A and 26B is different.

In other words, in the example shown in FIG. 10, the magnets 26A and 26B are provided with magnetic poles in a direction perpendicular to the optical axis O (therefore, magnetic poles in directions perpendicular to directions of magnetic poles of the magnets 24Aa, 24Ab, 24Ba and 24Bb), and are arranged so that, for example, the clockwise side is the S-pole, and the counterclockwise side is the N-pole around the optical axis O when the R direction is seen (see fields 1C and 2C).

However, the magnets 26A and 26B may be arranged so that, when the magnets 26A and 26B are seen in the R direction, the clockwise side is the N-pole, and the counterclockwise side is the S-pole around the optical axis O. Furthermore, similarly to the above description, the respective magnets 24Aa, 24Ab, 24Ba, 24Bb, 26A and 26B may be arranged so that all the polarities are reversed.

If such an arrangement is adopted, magnetic fields generated by the magnets 26A and 26B intersect magnetic fields generated by the magnets 24Aa, 24Ab, 24Ba and 24Bb, and, therefore, it becomes possible to cause the moving barrel 25 to slide without influencing the magnetic fields in a sliding direction generated by the magnets 24Aa, 24Ab, 24Ba and 24Bb of the magnetic actuator.

A field 1A(1) shows a state in which the moving barrel 25 is at a rest position on the F side. Similarly to the above description, at this time, as indicated by solid-line bi-directional arrows in the fields 1A and 1C, the S-pole of the magnet 24Aa and the N-pole of the magnet 26A exert magnetic attraction on each other, and the S-pole of the magnet 24B a and the N-pole of the magnet 26B exert magnetic attraction on each other, so that movement from the rest position is restricted, and the rest position is maintained even when a current is not flowing through the coils 23a and 23b.

It is also similar to the above description that, after that, a magnetic field is caused to be generated from the coil 23a to weaken the magnetic fields of the magnets 24Aa and 24Ba, and a magnetic field is caused to be generated from the coil 23b to strengthen the magnetic fields of the magnets 24Ab and 24Bb so that the moving barrel 25 is caused to move in the R direction.

A field 2A(2) shows a state at the time when the moving barrel 25 has moved a little in the R direction from the rest state in the field 1A(1). As seen when the field 2C is compared with the field 1C, the moving barrel 25 has rotated counterclockwise (counterclockwise when the R direction is seen) a little with the optical axis O as a central axis, from the state of (1), and a state has been obtained in which the N-pole of the magnet 24Aa and the S-pole of the magnet 26A are close to and face each other, and the N-pole of the magnet 24Ba and the S-pole of the magnet 26B are close to and face each other. Thereby, as indicated by solid-line bi-directional arrows in the fields 2A and 2C, the N-pole of the magnet 24Aa and the S-pole of the magnet 26A exert magnetic attraction on each other, and the N-pole of the magnet 24B a and the S-pole of the magnet 26B exert magnetic attraction on each other, so that the moving barrel 25 is restricted from rotating around the optical axis O and is prevented from inclining relative to the optical axis O.

A field 2B(3) shows a state at the time when the moving barrel 25 has further moved a little in the R direction from the state in the field 2A(2). At this time, as indicated by solid-line bi-directional arrows in the fields 2B and 2C, the N-pole of the magnet 24Ab and the S-pole of the magnet 26A exert magnetic attraction on each other, and the N-pole of the magnet 24Bb and the S-pole of the magnet 26B exert magnetic attraction on each other. Thereby, the moving barrel 25 is restricted from rotating around the optical axis O and is prevented from inclining relative to the optical axis O.

A field 1B(4) shows a state at the time when the moving barrel 25 has further moved in the R direction from the state in the field 2B(3) and reached a rest position on the R side. As seen when the field 1C is compared with the field 2C, the moving barrel 25 has rotated clockwise (clockwise rotation when the R direction is seen) a little with the optical axis as a central axis, from the state of (3), and a state has been obtained in which the S-pole of the magnet 24Ab and the N-pole of the magnet 26A are close to and face each other, and the S-pole of the magnet 24Bb and the N-pole of the magnet 26B are close to and face each other. Thereby, similarly to the above description, as indicated by solid-line bi-directional arrows in the fields 1B and 1C, the S-pole of the magnet 24Ab and the N-pole of the magnet 26A exert magnetic attraction on each other, and the S-pole of the magnet 24Bb and the N-pole of the magnet 26B exert magnetic attraction on each other, so that movement from the rest position is restricted, and the rest position is maintained even when a current is not flowing through the coils 23a and 23b.

In such a configuration, the moving barrel 25 rotates a little around the optical axis O when the state of (1) transitions to the state of (2), and the moving barrel 25 rotates a little around the optical axis O in an opposite direction when the state of (3) transitions to the state of (4). However, similarly to the above description, since the rotation positions of the moving barrel 25 around the optical axis O are the same in the states of (1) and (4) as shown in the field 1C, it is possible to prevent misalignment of the optical device at the two rest positions and restrict eccentricity to prevent degradation of the optical performance.

Similarly to the above description, movement of the moving barrel 25 from the rest position on the R side shown in the field 1B(4) to the rest position on the F side shown in the field 1A(1) is performed by applying a current in a direction opposite to the direction described above to the coils 23a and 23b, and it is possible to, since the rotation positions of the moving barrel 25 around the optical axis O are the same in the state of (4) and the state of (1), prevent misalignment of the optical device at the two rest positions and restrict eccentricity to prevent degradation of the optical performance.

Note that though FIG. 9 shows an example in which the magnet 26 (26A and 26B) arranged on the moving barrel 25 is provided with magnetic poles in the direction of the optical axis O, and FIG. 10 shows an example in which the magnet 26 is provided with magnetic poles in the circumferential direction with the optical axis O as a central axis, within a plane vertical to the optical axis O, the magnet 26 may be, regardless of the above examples, provided with magnetic poles in a radial direction with the optical axis O as a center, within the plane perpendicular to the optical axis O.

If examples of the above three are enumerated, the magnet 26, which is a moving barrel magnet, is arranged such that any direction, for example, among the direction of the optical axis O, the circumferential direction with the optical axis O as the central axis on the face perpendicular to the optical axis O, and the radial direction with the optical axis O as a center on the face perpendicular to the optical axis O is a magnetic pole array direction.

However, it is not prohibited to adopt another arrangement as the arrangement of the magnet 26.

According to the first embodiment as described above, since the magnet 24 (24A and 24B) arranged on the outer circumferential side of the fixed barrel 21 is provided on a part in the circumferential direction on the outer circumferential side of the coil 23 (a particular part in the circumferential direction) instead of being provided in the entire circumferential direction (360° around the optical axis O), it is possible to downsize the optical unit for endoscope 11 and, therefore, downsize the endoscope.

Further, since a magnetic body portion (the magnet 26 (26A and 26B) in the present embodiment) with magnetism stronger than the magnetism of the moving barrel 25 is arranged on a part in the circumferential direction of the moving barrel 25, corresponding to the magnet 24, it is possible to restrict rotation and inclination of the moving barrel 25 and reduce eccentricity of the optical device and sliding failure of the moving barrel 25.

Furthermore, since the magnet 24 includes the first and second magnets 24A and 24B at different positions in the circumferential directions, and the magnet 26 includes the magnet 26A and the magnet 26B at different positions in the circumferential directions, it is possible to more securely restrict rotation and inclination of the moving barrel 25 at the plurality of positions in the circumferential direction.

Since the coils 23a and 23b, the magnets 24Aa and 24Ab, and the magnets 24Ba and 24Bb are arranged at different positions along the optical axis O, it is possible to smoothly move the moving barrel 25 holding an optical device such as the lens 10b to two rest positions by the plurality of electromagnets.

In addition, if the magnet 26 (26A and 26B), which is a magnetic body portion, is arranged being buried below the outer circumferential face of the moving barrel 25 so that the magnet 26 (26A and 26B) does not come into contact with the inner circumferential face of the fixed barrel 21, it is possible to effectively prevent wear and damage of the magnet 26 (26A and 26B), which is configured of ceramic or the like, caused due to sliding on the fixed barrel 21. Thereby, it is possible to prevent fragments and powder of the magnet 26 from being caused by wear and damage and avoid occurrence of factors that degrade the optical performance of the objective optical system 10.

Further, since the magnets 26A and 26B, which are magnetic body portions, include the magnets 26Aa and 26Ba on the distal end side (the F side) and the magnets 26Ab and 26Bb on the proximal end side (the R side) that are arranged at different positions along the optical axis O, four magnetic poles exist on the moving barrel 25 in the direction of the optical axis O. Therefore, when the moving barrel 25 moves between a rest position on the F side and a rest position on the R side, the magnets 26A and 26B can mutually exert magnetic force with the magnets 24Aa, 24Ab, 24Ba and 24Bb of the fixed barrel 21 at a larger number of positions, and it is possible to more stably restrict rotation and inclination of the moving barrel 25 relative to the optical axis O.

By configuring a magnetic body portion with the magnet 26, it is possible to generate stable magnetic force irrespective of whether an external magnetic field exists or not, and restriction of rotation and inclination of the moving barrel 25 relative to the optical axis O becomes more stable. In this case, by disposing the magnet 26 in the recess portion 25a formed on the moving barrel 25, it is possible to attach the magnet 26 to the moving barrel 25 without damaging slidability of the moving barrel 25 relative to the fixed barrel 21.

Furthermore, since the magnetic pole array direction of the magnet 26 of the moving barrel 25 is any one direction among the direction of the optical axis O, the circumferential direction with the optical axis as a central axis and the radial direction with the optical axis as a center, it becomes easy to attach the magnet 26 to the moving barrel 25, and movement of the moving barrel 25 can be stabilized.

In addition, by arranging the optical unit for endoscope 11 described above on the distal end portion 5a of the insertion portion 5 of the endoscope 2, it is possible to obtain, for example, a small-size endoscope 2 capable of stably performing two-focus switching.

Second Embodiment

Figure 11:
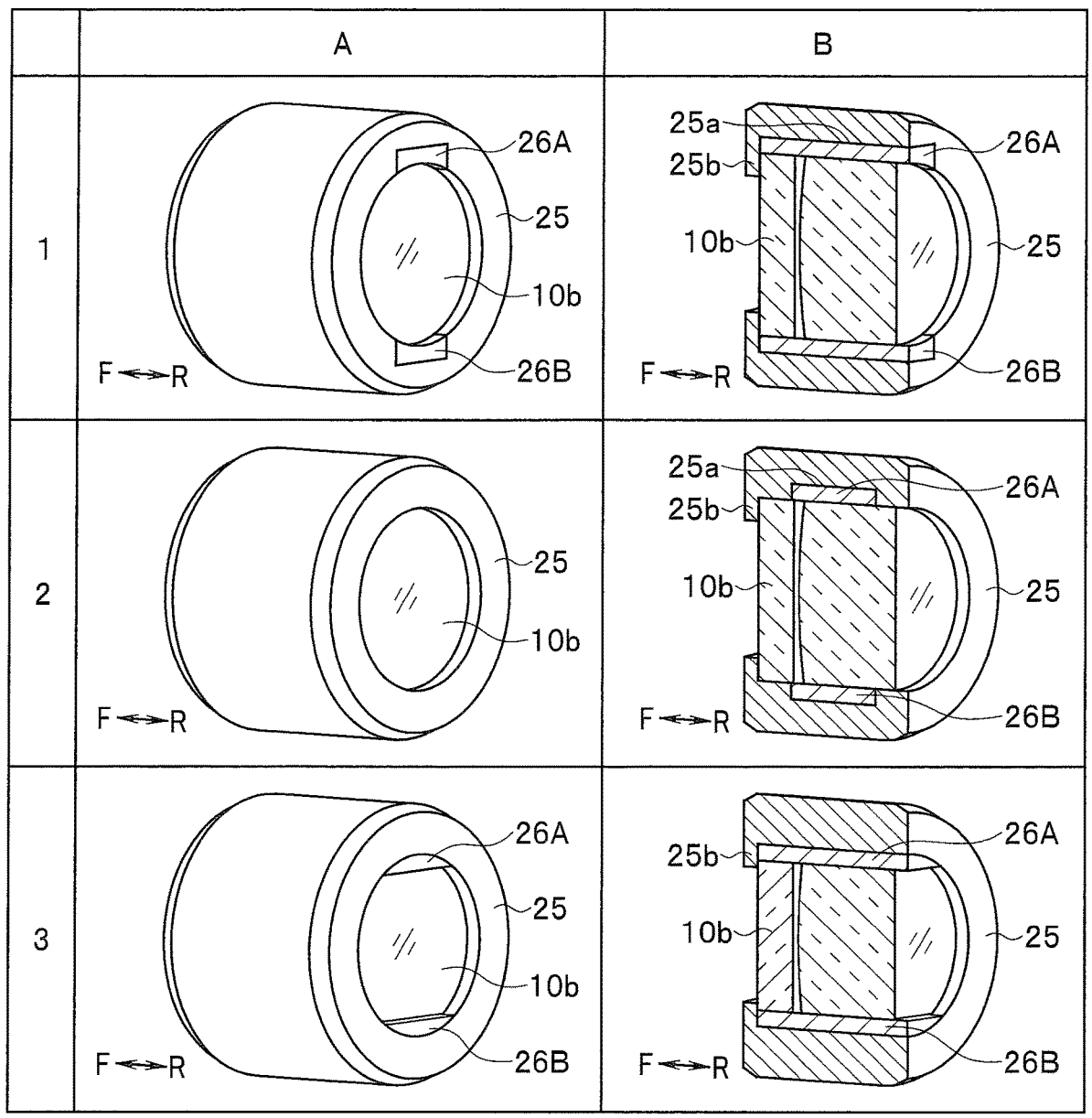
FIG. 11 is a diagram chart showing configuration examples of a magnetic body portion provided on a moving barrel in a second embodiment of the present invention.
Figure 12:
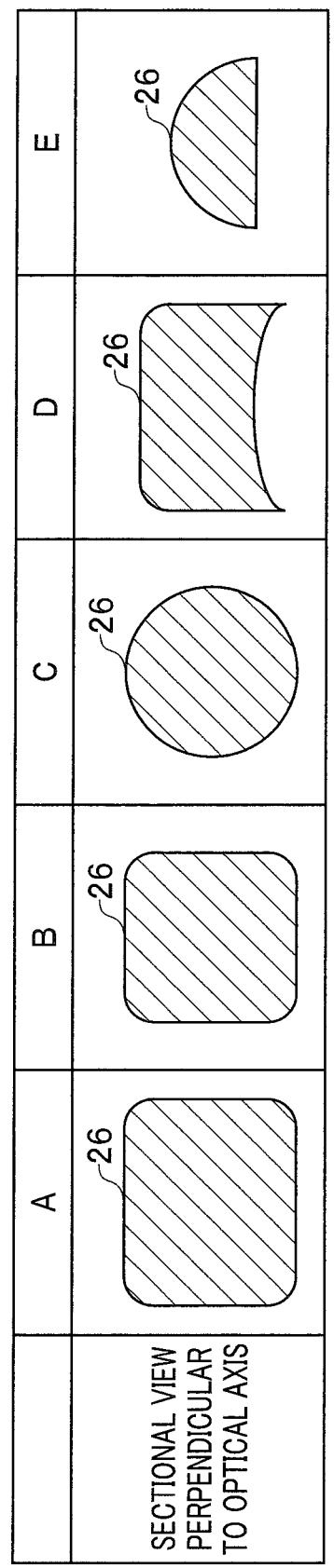
FIG. 12 is a diagram chart showing examples of a shape of a section of the magnetic body portion provided on the moving barrel, the section being perpendicular to an optical axis, in the second embodiment.

FIGS. 11 and 12 show a second embodiment of the present invention. In the second embodiment, for portions similar to portions of the first embodiment described above, the same reference numerals will be given, and description of the portions will be appropriately omitted. Mainly only different points will be described.

Though the magnet 26, which is a magnetic body portion, is arranged on the outer circumferential side of the moving barrel 25 in the first embodiment described above, the magnet 26 is arranged on the inner circumferential side of the moving barrel 25 in the present embodiment.

FIG. 11 is a diagram chart showing configuration examples of the magnetic body portion provided on the moving barrel 25. In FIG. 11, columns A and B show perspective views and sectional views in the direction of the optical axis O, respectively.

The magnets 26A and 26B shown in fields 1A and 1B are elongatedly provided in the direction of the optical axis O from the R side of an inner flange 25b provided on the F side of the moving barrel 25 to the R-side end face of the moving barrel 25. Faces on the inner diameter side (the optical axis O side) of the magnets 26A and 26B are formed in a cylindrical surface shape with the optical axis O as a central axis so that the faces constitute the same inner circumferential face as an inner circumferential face of the moving barrel 25. The magnets 26A and 26B are configured by being fixed in grooves in the direction of the optical axis O as the recess portions 25a formed on the inner circumferential face of the moving barrel 25 with adhesive or the like.

The magnets 26A and 26B shown in the fields 2A and 2B are configured by forming rectangular holes as the recess portions 25a in the middle in the direction of the optical axis O on the inner circumferential face of the moving barrel 25, and fitting the magnets 26A and 26B into the formed rectangular holes, respectively, and fixing the magnets 26A and 26B with adhesive or the like.

The magnets 26A and 26B shown in fields 3A and 3B are elongatedly provided in the direction of the optical axis O from the R side of the inner flange 25b provided on the F side of the moving barrel 25 to the R-side end face of the moving barrel 25 almost similarly to the configurations shown in the fields 1A and 1B. However, though the magnets 26A and 26B are arranged in the recess portions 25a formed on the inner circumferential face of the moving barrel 25 in the configuration shown in the fields 1A and 1B, the magnets 26A and 26B shown in the fields 3A and 3B are fixed on the inner circumferential face of the moving barrel 25 with adhesive or the like, that is, the magnets 26A and 26B are located inwardly from the inner circumferential face of the moving barrel 25. Therefore, an area around the lens 10b is downsized by an amount corresponding to a space where the magnets 26A and 26B are arranged. More specifically, an upper end side and a lower end side of the lens 10b are in a so-called D-cut shape.

Note that the inner circumferential face of the moving barrel 25 is a face where the lens 10b is arranged, and light from a subject passes along, the faces on the inner diameter side (the optical axis O side) of the magnets 26A and 26B are black surfaces (light reflection preventing surfaces) in order to restrict occurrence of flare and the like.

Note that, similarly to the first embodiment described above, in the case of arranging a plurality of magnets 26 on the moving barrel 25, it is desirable to unify positions where the respective magnets 26 are arranged, shapes of the respective magnets 26, lengths of the respective magnets 26 and the like.

FIG. 12 is a diagram chart showing examples of a shape of a section of the magnet 26 (26A and 26B), which is a magnetic body portion provided on the moving barrel 25, the section being perpendicular to the optical axis O. In FIG. 12, a lower side indicates an inner diameter side (the optical axis O side), and an upper side indicates an outer diameter side (the outer circumferential face side of the moving barrel 25).

A field A shows a section in a rectangular shape with rounded corners; a field B shows a section in a square shape with rounded corners; a field C shows a section in a circular shape; a field D shows a section the outer diameter side of which forms a rectangular shape with rounded corners and the inner diameter side of which forms an arc shape along the inner circumferential face of the moving barrel 25 (that is, along the outer circumferential face of the lens 10b); and a field E shows a section the outer diameter side of which forms an arc shape along the inner circumferential face of the moving barrel 25 and the inner diameter side of which forms a straight line along the D-cut of the lens 10b.

As for the magnet 26 in each of the fields A, B and D among the above fields, a groove or a hole with a rectangular-shaped section is formed on the inner circumferential face of the moving barrel 25, and the magnet 26 is fitted in the groove or the hole. As for the magnet 26 in the field C, a groove or a hole with a circular-shaped section is formed on the inner circumferential face of the moving barrel 25, and the magnet 26 is fitted in the groove or the hole. The magnet 26 in the field E can be immediately glued to the inner circumferential face of the moving barrel 25.

Note that though description has been made on the assumption that FIG. 12 shows shapes of the section of the magnet 26 perpendicular to the optical axis O, the shapes may be, regardless of this, shapes when the magnet 26 is seen from the outer diameter direction or the inner diameter direction. In addition, except for the point that the magnet 26 is arranged on the inner circumferential side of the moving barrel 25 instead of being arranged on the outer circumferential side, the shapes and arrangements of the magnet 26 described in the first embodiment described above (for example, such a configuration in which two magnets 26 are provided in the direction of the optical axis O, which is shown in the row 3 of FIG. 7) can be appropriately adopted for the magnet 26 of the second embodiment.

Therefore, similarly to the first embodiment described above, it is possible to flexibly adopt various kinds of shapes (or sizes or lengths) for the magnet 26, and the magnet 26 is hardly influenced by processability by selecting a shape in consideration of the processability. Furthermore, since it is possible to adopt various kinds of shapes (or sizes or lengths) for the magnet 26, there is an advantage that, even when the magnet 26 is arranged on the inner circumferential side of the moving barrel 25, optical design is hardly restricted.

According to the second embodiment as described above, effects almost similar to the effects of the first embodiment described above can be obtained; and, since the magnet 26, which is a magnetic body portion, is arranged on the inner circumferential side of the moving barrel 25, the magnets 26A and 26B do not come into contact with the inner circumferential face of the fixed barrel 21 when the moving barrel 25 moves, and it is possible to securely prevent wear and damage of the magnets 26A and 26B, which are configured of ceramic or the like, caused due to sliding on the fixed barrel 21.

Third Embodiment

Figure 13:
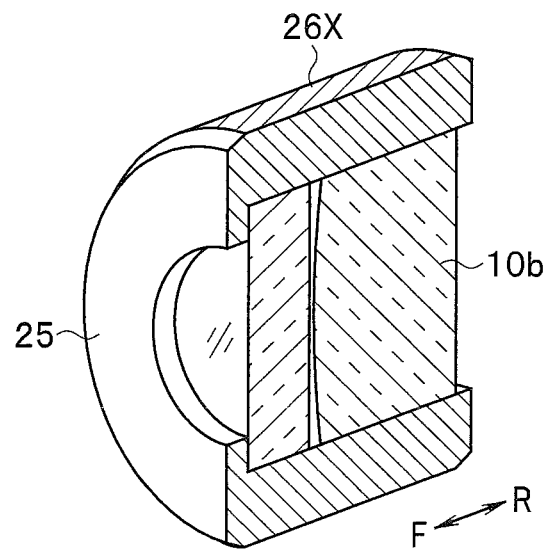
FIG. 13 is a sectional view in an optical axis direction showing a first example of a magnetic body portion provided on a moving barrel in a third embodiment of the present invention.
Figure 14:
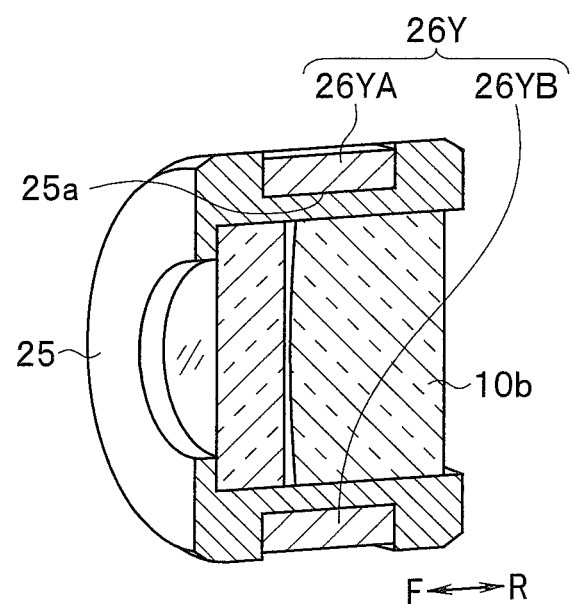
FIG. 14 is a sectional view in the optical axis direction showing a second example of the magnetic body portion provided on the moving barrel in the third embodiment.

FIGS. 13 and 14 show a third embodiment of the present invention. In the third embodiment, for portions similar to portions of the first and second embodiments described above, the same reference numerals will be given, and description of the portions will be appropriately omitted. Mainly only different points will be described.

Though a magnet is used as a component to cause the moving barrel 25 to be locally magnetized in the first and second embodiments described above, a ferromagnetic body member or surface treatment is used instead of a magnet in the present embodiment.

FIG. 13 is a sectional view in an optical axis direction showing a first example of a magnetic body portion provided on the moving barrel 25.

In the first example, a surface layer 26X configured of a ferromagnetic body is formed on a part in the circumferential direction of the moving barrel 25 as a magnetic body portion with magnetism stronger than the magnetism of the moving barrel 25. More specifically, plating by electroless nickel (Ni) boron (boron plating) is performed as surface treatment for magnetization. Otherwise, electrolytic nickel (Ni) plating or the like may be used instead. In the above cases, the surface layer 26X is a plated layer, but the surface treating is not limited to plating treatment.

Note that though the surface layer 26X is formed on the outer circumferential face of the moving barrel 25 in the example shown in FIG. 13, the surface layer 26X may be formed on the inner circumferential face of the moving barrel 25.

FIG. 14 is a sectional view in the optical axis direction showing a second example of the magnetic body portion provided on the moving barrel 25.

In the example shown in FIG. 14, a first ferromagnetic body 26YA is arranged as a first magnetic body portion at a first position in the circumferential direction of the moving barrel 25, and a second ferromagnetic body 26YB is arranged as a second magnetic body portion at a second position different from the first position in the circumferential direction of the moving barrel 25, as magnetic body portions with magnetism stronger than the magnetism of the moving barrel 25. The ferromagnetic bodies 26YA and 26YB are at the same position in the direction of the optical axis O.

As for a ferromagnetic body 26Y (26YA and 26YB are collectively referred to as 26Y), rectangular holes are formed as the recess portions 25a in the middles of the outer circumferential face of the moving barrel 25 in the direction of the optical axis O, and the ferromagnetic body 26Y (26YA and 26YB are collectively referred to as 26Y) fitted into the formed rectangular holes and fixed with adhesive or the like. Other configurations (for example, a configuration in which the surfaces are flat) of the ferromagnetic body 26Y shown in FIG. 14 are almost similar to the configurations of the magnets 26A and 26B shown in the fields 2A and 2B of FIG. 7.

Note that, for the ferromagnetic body 26Y, an arbitrary shape or arrangement among the various kinds of shapes and arrangements of the magnet 26 described in detail in the first and second embodiments described above may be adopted (therefore, the ferromagnetic body 26Y may be arranged on the inner circumferential side of the moving barrel 25).

Furthermore, configuration of a magnetic body portion is not limited to adopting any of the magnet 26, the surface layer 26X and the ferromagnetic body 26Y. The magnetic body portion may be configured by appropriately combining the above to restrict rotation of the moving barrel 25.

According to the third embodiment as described above, effects almost similar to the effects of the first and second embodiments described above can be obtained, and it is also possible to, by providing a ferromagnetic body on the moving barrel 25 as magnetic body portions, restrict rotation and inclination of the moving barrel 25 because the ferromagnetic body is attracted to the magnet 24 (24A and 24B) of the fixed barrel 21.

In this case, by using the ferromagnetic body 26Y as magnetic body portions, it is possible to, at the time of disposing the ferromagnetic body 26Y in the recess portions 25a of the moving barrel 25 formed by a soft magnetic body member, easily perform the attachment work without magnetic attraction working unlike the magnet 26.

Further, in the case of using the surface layer 26X configured of a ferromagnetic body, a magnetic body portion can be formed only by performing a plating process, and it is possible to omit a process for mechanically forming the recess portions 25a.

Related Embodiment

Figure 15:
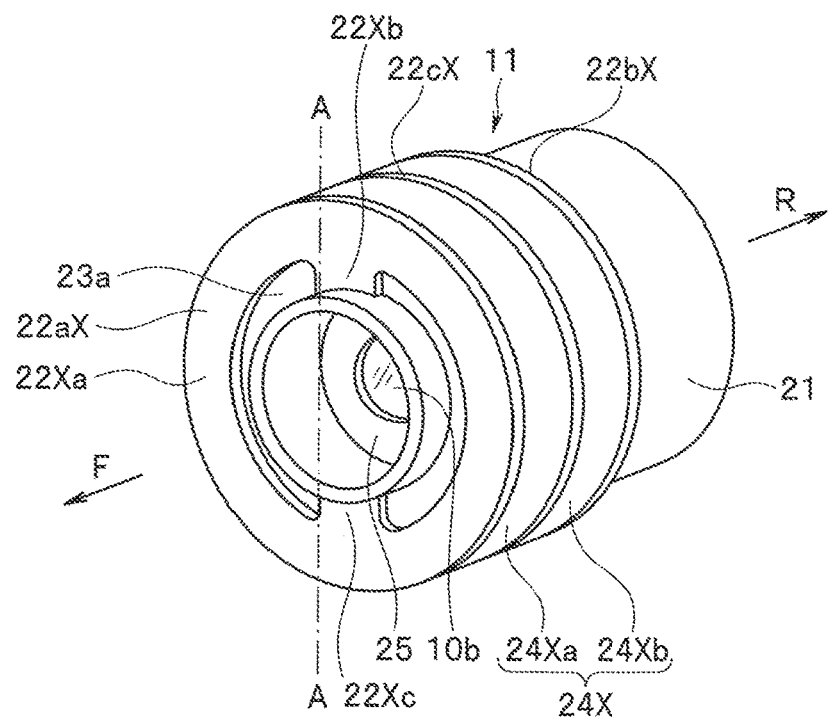
FIG. 15 is a perspective view showing a configuration example of an optical unit for endoscope in an embodiment related to the present invention.
Figure 16:
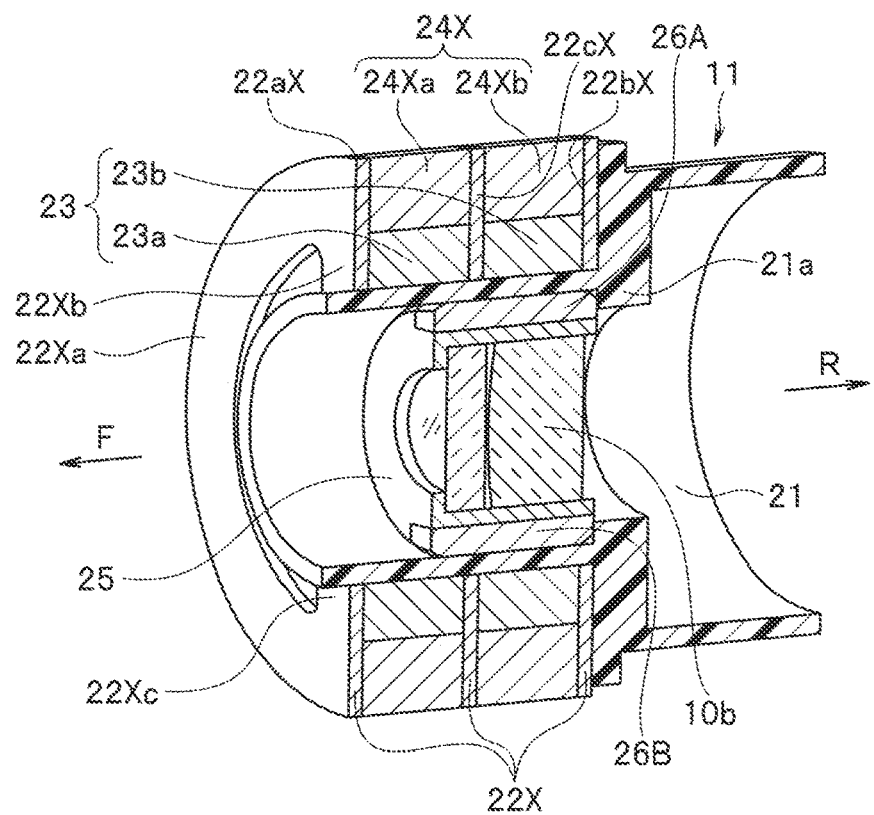
FIG. 16 is a diagram showing an A-A section of the optical unit for endoscope in FIG. 15 in the related embodiment.

FIGS. 15 and 16 show an embodiment related to the present invention. FIG. 15 is a perspective view showing a configuration example of the optical unit for endoscope 11; and FIG. 16 is a diagram showing an A-A section of the optical unit for endoscope 11 in FIG. 15.

In the related embodiment, for portions similar to portions of the first to third embodiments described above, the same reference numerals will be given, and description of the portions will be appropriately omitted. Mainly only different points will be described.

Though the magnet 24 (24A and 24B) arranged on the outer circumferential side of the fixed barrel 21 is provided on a part (a particular part) in the circumferential direction in the first to third embodiments described above, the configuration to restrict rotation and inclination of a moving barrel is not limited to the above. For example, in a configuration in which a magnet 24X is provided in the entire circumferential direction (360° around the optical axis O) on the outer circumferential side of the coil 23, it is also possible to restrict rotation and inclination of a moving barrel to reduce eccentricity of an optical device and sliding failure of the moving barrel. An example of such a configuration will be described in the related embodiment.

The optical unit for endoscope 11 of the present embodiment is different, for example, from the configuration of the first embodiment shown in FIG. 5 in the following points.

The magnet 24X forms a ring shape and provided in the entire circumferential direction (360° around the optical axis O) on the outer circumferential side of the coil 23.

In the example shown in FIGS. 15 and 16, the magnet 24X includes a first magnet 24Xa arranged on the outer circumferential side of the first coil 23a (the F side) and a second magnet 24Xb arranged on the outer circumferential side of the second coil 23b (the R side).

Furthermore, yokes (collectively referred to "the yokes" 22X) sandwiching the coil 23 and the magnet 24X are formed by magnetic bodies in a substantially doughnut-disk shape, being separated by a predetermined distance along the optical axis O of the optical device, and each of the yokes 22X is provided with a ring-shaped doughnut-disk portion 22Xa.

The doughnut-disk portion 22Xa is configured so that an outer diameter is almost the same as an outer diameter of the magnet 24X (the outer diameter may be the same as or somewhat larger/smaller than the outer diameter of the magnet 24X), and an inner diameter is larger than an outer diameter of a part of the fixed barrel 21 where the coil 23 is wound (or an inner diameter of the coil 23).

Furthermore, each of the yokes 22X is provided with an inner projecting portion projecting in an inner diameter direction from a part of the doughnut-disk portion 22Xa in a circumferential direction, and the yokes 22X are configured so that only the inner projecting portion provided on a part in the circumferential direction comes into contact with the outer surface of the fixed barrel 21, and a part other than the projecting portion is separated from the outer surface of the fixed barrel 21.

In the example shown in FIGS. 15 and 16, the inner projecting portion includes a first inner projecting portion 22Xb arranged at a first position in the circumferential direction and a second inner projecting portion 22Xc arranged at a second position different from the first position in the circumferential direction. More specifically, the first and second inner projecting portion 22Xb and 22Xc are arranged at positions different by 180° in the circumferential direction.

In the example shown in FIGS. 15 and 16, according to a configuration in which the coil 23 includes the first and second coils 23a and 23b arranged at different position along the optical axis between the first yoke 22aX and the second yoke 22bX, and the magnet 24X includes the first magnet 24Xa arranged on the outer circumferential side of the first coil 23a and the second magnet 24Xb arranged on the outer circumferential side of the second coil 23b, a third yoke 22cX is further provided.

The third yoke 22cX is arranged between the first coil 23a and the first magnet 24Xa, and the second coil 23b and the second magnet 24Xb on the outer surface of the fixed barrel 21, configured similarly to the first yoke 22aX and the second yoke 22bX and provided with the first and second inner projecting portions 22Xb and 22Xc. Therefore, as for the third yoke 22cX, similarly to the first yoke 22aX and the second yoke 22bX, only the first and second inner projecting portions 22Xb and 22Xc come into contact with the outer surface of the fixed barrel 21, and a part other than the first and second inner projecting portions 22Xb and 22Xc is separated from the outer surface of the fixed barrel 21.

Note that though a configuration is assumed in the above description in which the coil 23 includes the first and second coils 23a and 23b, and the magnet 24X includes the first and second magnets 24Xa and 24Xb, a configuration is also possible, regardless of the above, which includes one coil 23 and one magnet 24X (therefore, a configuration in which the third yoke 22cX is omitted) almost similarly to the basic configuration described with reference to FIG. 3 and the like.

Further, though description has been made above on the assumption that the magnet 24X is configured to form a ring shape, the magnet 24X may be configured being provided on a part in the circumferential direction similarly to the first to third embodiments described above. In this case, by reducing a width of the doughnut-disk portion 22Xa in the radial direction except the part where the magnet 24 (24A and 24B) is arranged, it is possible to contribute to downsizing of the whole apparatus.

Furthermore, though two inner projecting portions (the first and second inner projecting portion 22Xb and 22Xc) are provided on the yokes 22X in the above description, a configuration is also possible, regardless of the above, in which only one inner projecting portion is provided similarly to the basic configuration described with reference to FIG. 3 and the like. In this case, a spacer or the like formed by a non-magnetic body can be appropriately used to separate a part of the yokes 22X other than the inner projecting portion from the outer surface of the fixed barrel 21.

As for configurations of the magnet 26 (26A and 26B), the surface layer 26X and the ferromagnetic body 26Y arranged on the moving barrel 25, configurations in the first to third embodiments such as the configurations in FIGS. 7 and 8, FIGS. 11 to 14, and the like can be appropriately applied.

Operation of the optical unit for endoscope 11 in such a configuration is almost similar to the operation described with reference to FIG. 4, 9 or 10 except for a point that a main passage route of magnetic force lines generated from the magnet 24X is a route passing through the inner projecting portions 22Xb and 22Xc of the yokes 22X.

For example, a case where magnetic force lines of the first magnet 24Xa the F-side and the R-side of which are magnetized to the N-pole and the S-pole, respectively, pass through the moving barrel 25 existing at a rest position on the F side will be described. The magnetic force lines starting from the N-pole of the first magnet 24Xa concentratedly enter, for example, the first yoke 22aX that is in contact with the N-pole of the first magnet 24Xa, pass through the fixed barrel 21, which is a non-magnetic body, from the inner projecting portions 22Xb and 22Xc of the first yoke 22aX, and reach the F side of the moving barrel 25 which is a soft magnetic body. At this time, the F side of the moving barrel 25 is magnetized to the S-pole, and the R side is magnetized to the N-pole. After that, the magnetic force lines start from the R side of the moving barrel 25, pass through the fixed barrel 21, which is a non-magnetic body, concentratedly enter the inner projecting portions 22Xb and 22Xc of the third yoke 22cX that is in contact with the S-pole of the first magnet 24Xa, enter the S-pole of the first magnet 24Xa from the third yoke 22cX, the S-pole being an end point. Almost the same goes for a passage route of magnetic force lines of the second magnet 24Xb.

According to the related embodiment as described above, effects almost similar to the effects of the first to third embodiments described above can be obtained. In addition, since only the inner projecting portions provided on a part of the yokes 22X in the circumferential direction come into contact with the outer surface of the fixed barrel 21, and a part other than the inner projecting portions is separated from the outer surface of the fixed barrel, it becomes possible to use, for example, the magnet 24X forming a ring shape similar to a conventional magnet, and it is possible to obtain magnetic force stronger than a case where the magnet 24 (24A and 24B) is provided only on a part in the circumferential direction.

Further, since the first and second projecting portions 22Xb and 22Xc at different positions in the circumferential direction are provided as inner projecting portions, it is possible to more securely restrict rotation and inclination of the moving barrel 25 at the plurality of positions in the circumferential direction.

Furthermore, since the first coil 23*a* and the first magnet 24X*a*, and the second coil 23*b* and the second magnet 24X*b* are provided at different positions along the optical axis, it is possible to smoothly move the moving barrel 25 holding an optical device such as lens 10*b* to two rest positions by the plurality of electromagnets.

According to the related embodiment as described above, configurations as shown in the following supplementary note items can be obtained.

[Supplementary Note 1]

An optical unit for endoscope including:

a moving barrel which is a soft magnetic body, configured to hold an optical device;

a fixed barrel which is a non-magnetic body, configured to movably hold the moving barrel on an inner circumferential face;

a first yoke and a second yoke arranged on an outer surface of the fixed barrel, being separated from each other by a predetermined distance along an optical axis of the optical device, only an inner projecting portion of each of the first yoke and the second yoke provided on a part in a circumferential direction coming into contact with the outer surface of the fixed barrel, and a part other than the inner projecting portion being separated from the outer surface of the fixed barrel;

a coil formed being wound around the outer surface of the fixed barrel between the first yoke and the second yoke, with the optical axis as a central axis;

a magnet arranged on an outer circumferential side of the coil between the first yoke and the second yoke; and a magnetic body member with magnetism stronger than magnetism of the moving barrel, the magnetic body member being arranged on a part of the moving barrel in a circumferential direction, corresponding to the inner projecting portion; wherein as for each of the optical device, the coil, the magnet and the magnetic body member, at least one is provided.

[Supplementary Note 2]

The optical unit for endoscope according to supplementary note 1, wherein the inner projecting portion includes a first inner projecting portion arranged at a first position in a circumferential direction and a second inner projecting portion arranged at a second position different from the first position in the circumferential direction;

the magnetic body member includes a first magnetic body member arranged at a first position in the circumferential direction of the moving barrel, corresponding to the first inner projecting portion, and a second magnetic body member arranged at a second position different from the first position in the circumferential direction of the moving barrel, corresponding to the second inner projecting portion; and as for each of the first magnetic body member and the second magnetic body member, at least one is provided.

[Supplementary Note 3]

The optical unit for endoscope according to supplementary note 2, wherein the coil includes a first coil and a second coil arranged at different positions along the optical axis between the first yoke and the second yoke;

the magnet includes a first magnet arranged on an outer circumferential side of the first coil and a second magnet arranged on an outer circumferential side of the second coil; and the optical unit for endoscope further includes a third yoke arranged between the first coil and the first magnet, and the second coil and the second magnet on the outer surface of the fixed barrel, and provided with the first inner projecting portion and the second inner projecting portion.

[Supplementary Note 4]

The optical unit for endoscope according to supplementary note 1, wherein the magnetic body member is arranged being buried below an outer circumferential face of the moving barrel so as not to come into contact with the inner circumferential face of the fixed barrel.

[Supplementary Note 5]

The optical unit for endoscope according to supplementary note 1, wherein the magnetic body member is arranged on an inner circumferential side of the moving barrel.

[Supplementary Note 6]

The optical unit for endoscope according to supplementary note 1, wherein the magnetic body member includes a distal-end-side magnetic body member and a proximal-end-side magnetic body member arranged at different positions along the optical axis on the moving barrel.

[Supplementary Note 7]

The optical unit for endoscope according to supplementary note 1, wherein the magnetic body member includes a moving barrel magnet disposed on the moving barrel.

[Supplementary Note 8]

The optical unit for endoscope according to supplementary note 7, wherein the moving barrel magnet is arranged so that any one direction, among a direction of the optical axis, a circumferential direction with the optical axis as a center, on a plane perpendicular to the optical axis, and a radial direction with the optical axis as the center, on the plane perpendicular to the optical axis, is a magnetic pole array direction.

[Supplementary Note 9]

The optical unit for endoscope according to supplementary note 1, wherein the magnetic body member includes a ferromagnetic body disposed on the moving barrel.

[Supplementary Note 10]

The optical unit for endoscope according to supplementary note 1, wherein the magnetic body member includes a surface layer configured of a ferromagnetic body, the surface layer being formed on the moving barrel.

[Supplementary Note 11]

An endoscope including an insertion portion with the optical unit for endoscope according to supplementary note 1 arranged on a distal end portion.

Note that the present invention is not limited to the embodiments described above as they are, and it is possible to, at an implementation stage, modify components to embody the invention within a range not departing from the spirit of the invention. Further, various kinds of aspects of the invention can be formed by appropriately combining a plurality of components disclosed in the above embodiments. For example, some components may be deleted from all the components shown in the embodiments. Furthermore, components among different embodiments may be appropriately combined. Thus, various kinds of modifications and applications are, of course, possible within the range not departing from the spirit of the invention.

What is claimed is:

1. An optical unit comprising:
a fixed body comprising a non-magnetic material, the fixed body comprising an inner surface and an outer surface;
a moving body movable relative to the fixed body within the inner surface, the moving body comprising a soft magnetic material having a first magnetism, the moving body being configured to hold an optical device;

a first yoke and a second yoke arranged on the outer surface of the fixed body, the first yoke being separated from the second yoke in an optical axis direction of the optical device;

a coil wound around the outer surface of the fixed body and being disposed between the first yoke and the second yoke;

a magnet arranged at a position only on a partial portion of an outer surface of the coil and being disposed between the first yoke and the second yoke; and a magnetic body having a second magnetism stronger than the first magnetism of the moving body, the magnetic body being arranged only on a partial portion of the moving body so as to be aligned in a direction perpendicular to the optical axis direction with the position of the magnet when viewed in a cross-section of the moving body taken perpendicular to the optical axis direction.

2. The optical unit according to claim 1, wherein:
the magnet comprises a first magnet and the position comprises a first position, and
the magnetic body comprising a first magnetic body aligned in the direction perpendicular to the optical axis direction with the first position of the first magnet;
the optical unit further comprises:
a second magnet arranged at a second position different from the first position on the outer surface of the coil and being disposed between the first yoke and the second yoke; and
a second magnetic body arranged on the moving body so as to be aligned in the direction perpendicular to the optical axis direction with the second position of the second magnet.

3. The optical unit according to claim 2, wherein:
the coil comprises a first coil arranged at a first longitudinal position in the optical axis direction between the first yoke and the second yoke;
the first magnet comprises a first-first magnet arranged at the first longitudinal position and a first-second magnet arranged at the second longitudinal position; and
the second magnet comprises a second-first magnet arranged at the first longitudinal position and a second-second magnet arranged at the second longitudinal position.

4. The optical unit according to claim 3, further comprising a third yoke arranged on the outer surface of the fixed body between the first yoke and the second yoke,
wherein the third yoke is disposed between the first coil and the second coil.

5. The optical unit according to claim 1, wherein
the moving body comprises a recess on an outer surface of the moving body, and
the magnetic body is at least partially disposed within the recess such that an outer surface of the magnetic body in the direction perpendicular to the optical axis direction does not interfere with the inner surface of the fixed body.

6. The optical unit according to claim 1, wherein the magnetic body is arranged on an inner circumferential side of the moving body.

7. The optical unit according to claim 1, wherein the magnetic body comprises a distal-end-side magnetic body and a proximal-end-side magnetic body arranged at different longitudinal positions along the optical axis direction of the moving body.

8. The optical unit according to claim 1, wherein:
the moving body comprises a recess on an outer surface of the moving body, and
the magnetic body is at least partially disposed within the recess.

9. The optical unit according to claim 8, wherein a magnetic pole array direction of the magnetic body is arranged in one or more of longitudinally in the optical axis direction, a circumferential direction around an optical axis, or the direction perpendicular to the optical axis direction.

10. The optical unit according to claim 1, wherein the magnetic body comprises a ferromagnetic body.

11. The optical unit according to claim 1, wherein the magnetic body comprises a surface layer configured of a ferromagnetic body, the surface layer being formed as a portion of the moving body.

12. An endoscope comprising:
an insertion portion; and
the optical unit according to claim 1 arranged on a distal end portion of the insertion portion.

13. The optical unit according to claim 1, wherein
the magnet and the magnetic body are disposed extending along the optical axis direction, and
the magnet and the magnetic body oppose each other through the coil and the fixed body.

14. The optical unit according to claim 1, wherein the magnet and the magnetic body are each disposed on a same cross-sectional plane perpendicular to the optical axis.

15. The optical unit according to claim 1, wherein an inner surface of the magnet and an outer surface of the magnetic body oppose each other in the direction perpendicular to the optical axis direction.

16. The optical unit according to claim 1, wherein the fixed body comprising an inner flange, the inner flange being configured to abut the moving body to limit a movement of the moving body relative to the fixed body in the optical axis direction.

17. The optical unit according to claim 16, wherein a proximal end of the magnet is disposed distally relative to the inner flange.

18. The optical unit according to claim 1, wherein the magnet is formed as a plate, and the magnet extending fully from the first yoke to the second yoke.

19. The optical unit according to claim 1, wherein:
the first yoke having a first protrusion partially formed on a first outer surface of the first yoke;
the second yoke having a second protrusion partially formed on a first outer surface of the second yoke; and
the first protrusion and the second protrusion sandwich the magnet therebetween in the optical axis direction.

20. The optical unit according to claim 19, wherein a circumferential width of the first protrusion and a circumferential width the second protrusion are each larger than a circumferential width of the magnet.

* * * * *